(12) United States Patent
Fukuda

(10) Patent No.: US 10,342,499 B2
(45) Date of Patent: Jul. 9, 2019

(54) TOMOGRAPHIC IMAGE GENERATION DEVICE, METHOD AND RECORDING MEDIUM

(71) Applicant: FUJIFILM Corporation, Tokyo (JP)

(72) Inventor: Wataru Fukuda, Ashigarakami-gun (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 145 days.

(21) Appl. No.: 15/262,215

(22) Filed: Sep. 12, 2016

(65) Prior Publication Data

US 2017/0071554 A1 Mar. 16, 2017

(30) Foreign Application Priority Data

Sep. 16, 2015 (JP) .................. 2015-183042

(51) Int. Cl.
*G06T 11/00* (2006.01)
*A61B 6/00* (2006.01)
(Continued)

(52) U.S. Cl.
CPC .............. *A61B 6/502* (2013.01); *A61B 6/025* (2013.01); *A61B 6/4452* (2013.01); *A61B 6/463* (2013.01); *A61B 6/5205* (2013.01); *G06T 11/006* (2013.01); *A61B 6/027* (2013.01); *A61B 6/0414* (2013.01); *A61B 6/4291* (2013.01)

(58) Field of Classification Search
CPC ....... A61B 6/032; A61B 6/025; A61B 6/4085; A61B 5/0095; A61B 8/5207; A61B 8/13; A61B 8/0825; G06T 11/006; G06T 11/005; G06T 2211/421; G06T 2207/10081; G06T 11/003; G06T 2207/10072; G06T 7/0012; G06T 2207/10132; G06T 5/002; G06T 11/008; G06T 2207/20016; G06T 2207/20064; G06T 2207/30004
See application file for complete search history.

(56) References Cited

U.S. PATENT DOCUMENTS

| 4,313,163 A * | 1/1982 | Mizutani ................ A61B 6/032 378/14 |
| 5,920,660 A * | 7/1999 | Goto ..................... G06T 11/005 382/291 |

(Continued)

FOREIGN PATENT DOCUMENTS

| JP | 2013-000261 A | 1/2013 |
| JP | 2013-031641 A | 2/2013 |

*Primary Examiner* — Andrew M Moyer
*Assistant Examiner* — Dennis Rosario
(74) *Attorney, Agent, or Firm* — Sughrue Mion, PLLC

(57) ABSTRACT

An image obtaining unit obtains a plurality of projection images taken by imaging a subject with different radiation source positions. A frequency decomposition unit performs frequency decomposition on each of the projection images to obtain a plurality of band projection images representing frequency components for individual frequency bands for each of the projection images. A reconstruction unit reconstructs the band projection images to generate band tomographic images of the subject for the individual frequency bands. A frequency synthesis unit performs frequency synthesis on the band tomographic images to generate a tomographic image of the subject.

22 Claims, 16 Drawing Sheets

(51) Int. Cl.
*A61B 6/02* (2006.01)
*A61B 6/04* (2006.01)

(56) References Cited

U.S. PATENT DOCUMENTS

| | | | | |
|---|---|---|---|---|
| 6,333,960 B1* | 12/2001 | Tam | ............... | A61B 6/032 |
| | | | | 378/15 |
| 6,697,508 B2* | 2/2004 | Nelson | ............... | G06T 11/006 |
| | | | | 378/4 |
| 7,106,825 B2* | 9/2006 | Gregerson | ............... | G06T 11/005 |
| | | | | 378/19 |
| 7,227,982 B2* | 6/2007 | De Man | ............... | G06T 11/006 |
| | | | | 378/62 |
| 7,369,691 B2* | 5/2008 | Kondo | ............... | G06T 15/08 |
| | | | | 382/128 |
| 8,116,426 B2* | 2/2012 | Hein | ............... | G06T 11/005 |
| | | | | 378/19 |
| 8,642,968 B2* | 2/2014 | Akahori | ............... | G06T 11/005 |
| | | | | 250/363.02 |
| 8,660,330 B2* | 2/2014 | Jarisch | ............... | G06T 11/006 |
| | | | | 378/21 |
| 9,002,090 B2* | 4/2015 | Koehler | ............... | G06T 11/008 |
| | | | | 382/131 |
| 9,418,417 B2* | 8/2016 | Kobayashi | ............... | G06T 7/0012 |
| 9,713,450 B2* | 7/2017 | Claus | ............... | A61B 6/032 |
| 2012/0321163 A1 | 12/2012 | Akahori | | |
| 2013/0051516 A1* | 2/2013 | Yang | ............... | A61B 6/03 |
| | | | | 378/4 |
| 2015/0317820 A1* | 11/2015 | Choi | ............... | G06T 15/08 |
| | | | | 382/132 |
| 2017/0053402 A1* | 2/2017 | Migukin | ............... | G01R 33/5611 |

\* cited by examiner

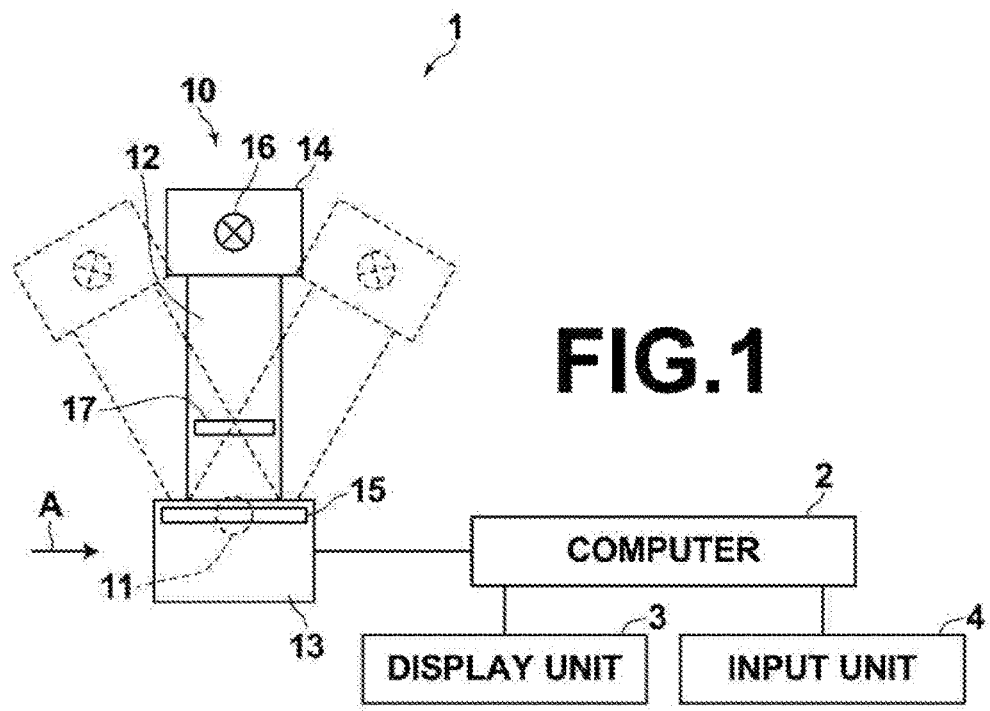
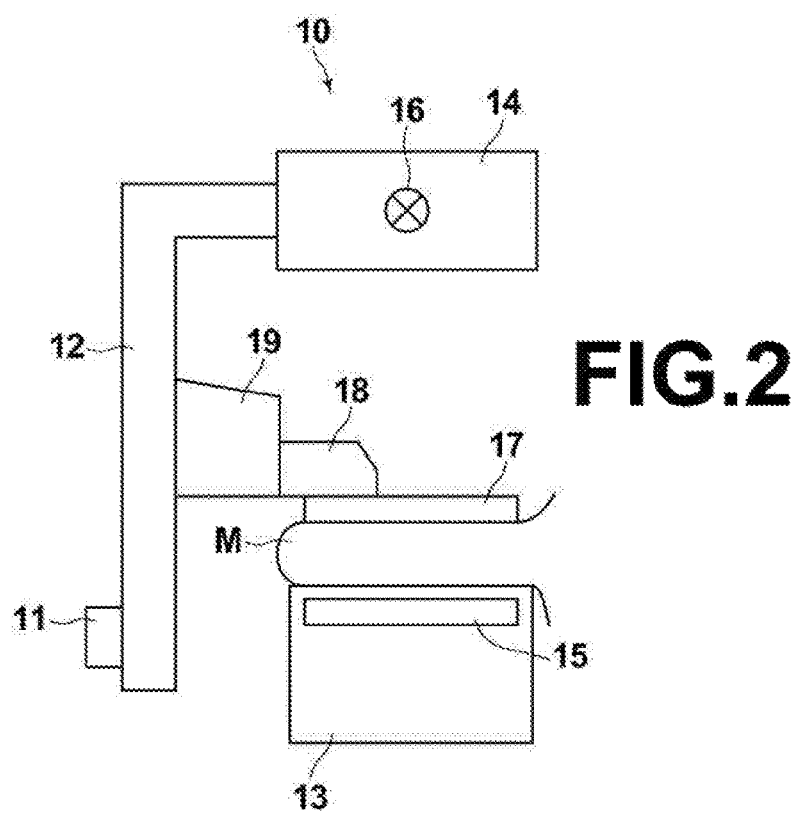

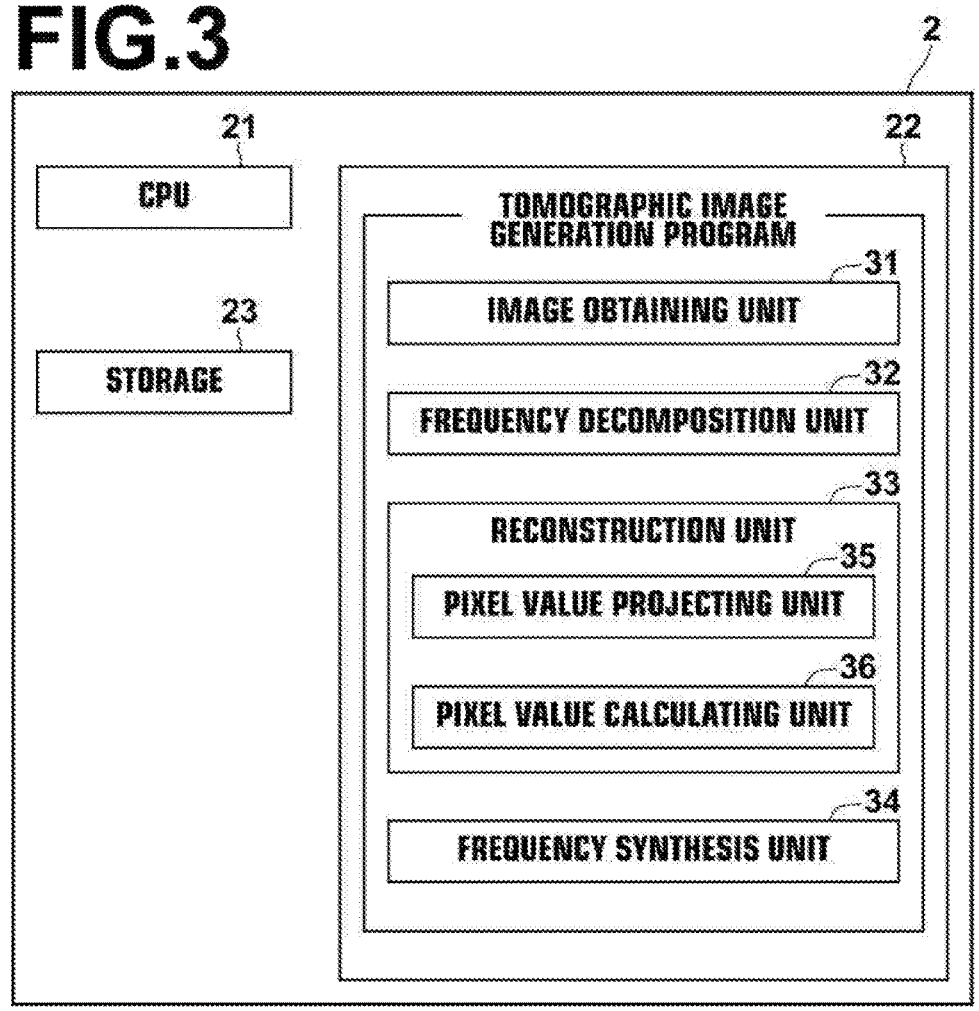

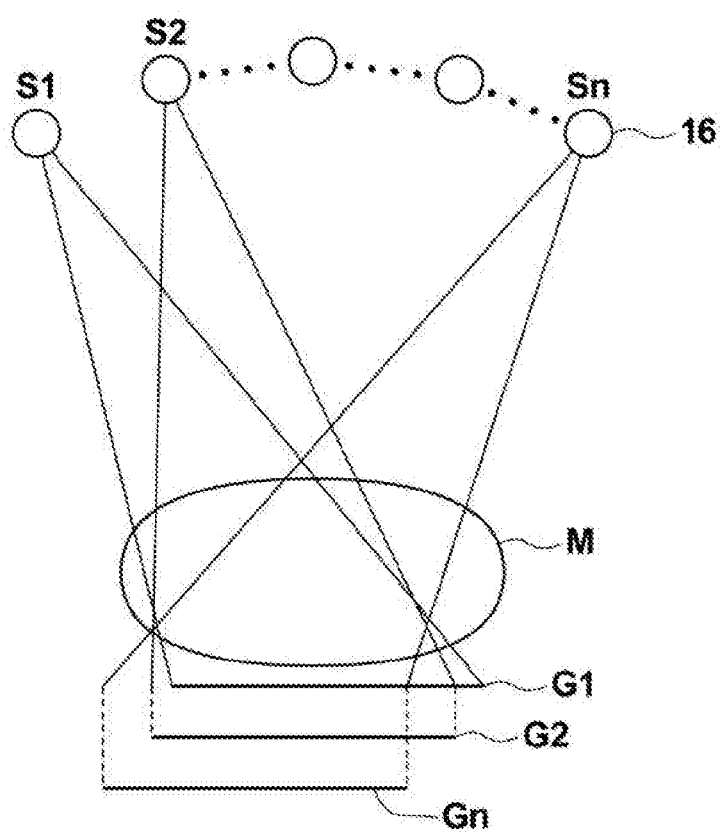

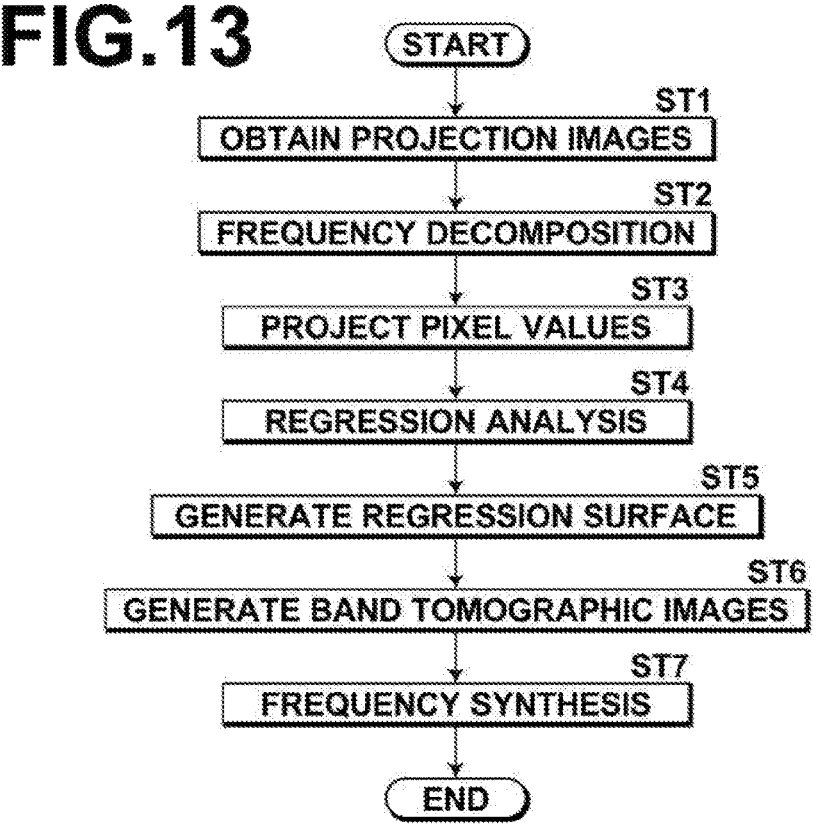
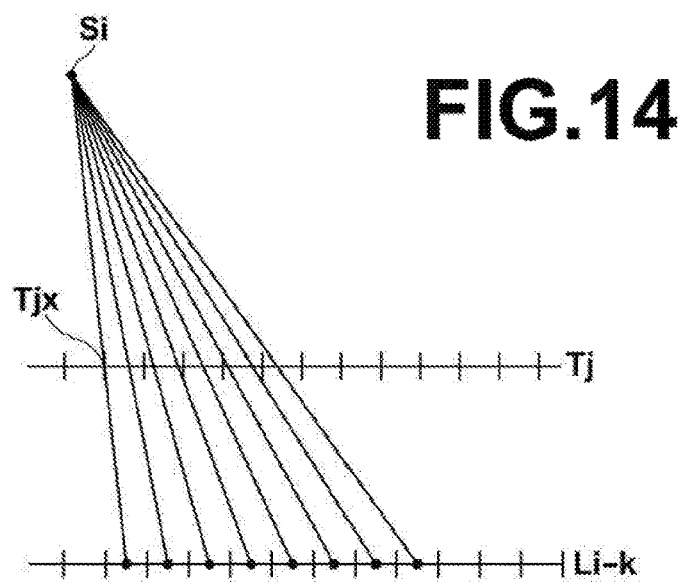

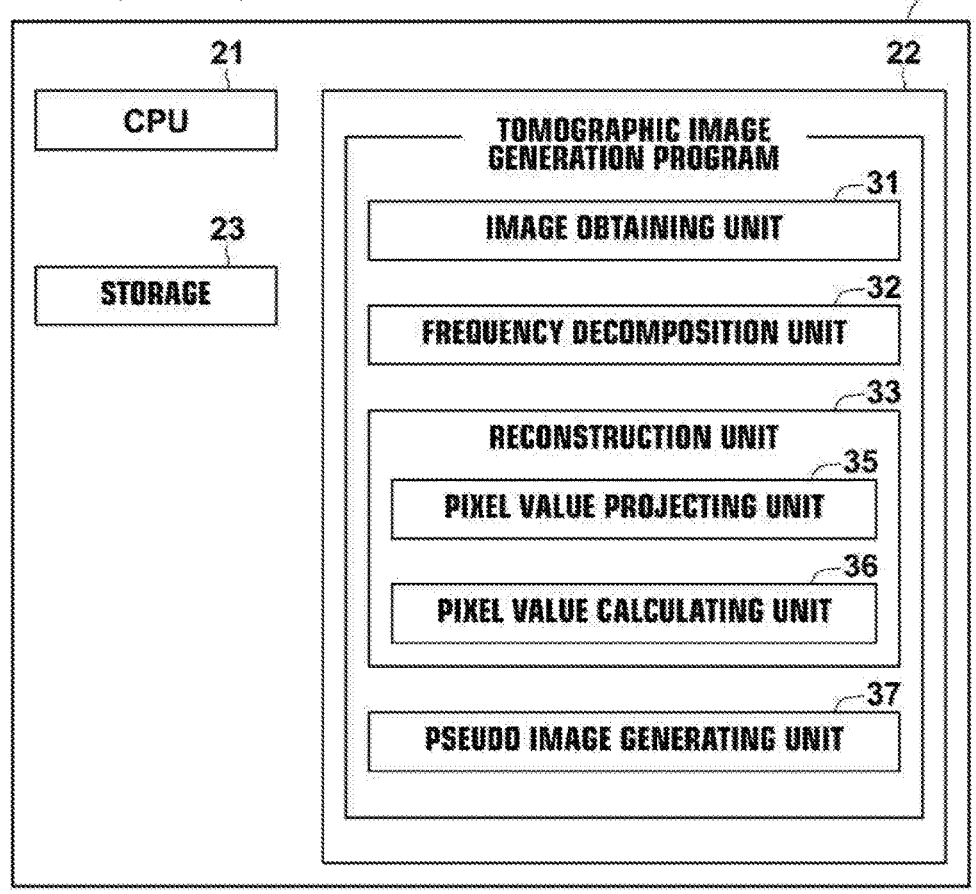
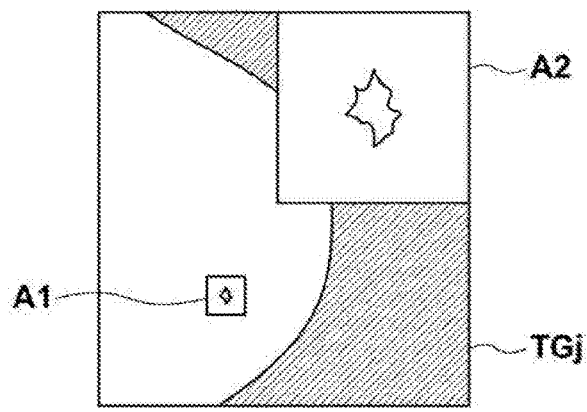

TOMOGRAPHIC IMAGE GENERATION DEVICE, METHOD AND RECORDING MEDIUM

CROSS-REFERENCE TO RELATED APPLICATIONS

The present application claims priority under 35 U.S.C. § 119 to Japanese Patent Application No. 2015-183042, filed on Sep. 16, 2015. The above application is hereby expressly incorporated by reference, in its entirety, into the present application.

BACKGROUND

The present disclosure relates to a tomographic image generation device, a tomographic image generation method and a tomographic image generation program for generating a tomographic image from a plurality of projection images of a subject, which are obtained by imaging the subject with different radiation source positions.

In recent years, in order to more closely observe an affected part of the body with a radiographic imaging apparatus using radiation, such as x-ray or γ-ray, tomosynthesis imaging has been proposed, in which imaging is performed by applying radiation to the subject from different radiation source positions by moving the radiation source, and a tomographic image where a desired slice plane is emphasized is generated from the thus obtained projection images. In the tomosynthesis imaging, a plurality of projection images are obtained by imaging a subject with different radiation source positions by moving the radiation source in parallel with the radiation detector or along a circular or ellipsoidal arc trajectory depending on characteristics of the imaging apparatus and necessary tomographic images, and the projection images are reconstructed to generate a tomographic image using a shift-and-add method, or a back projection method such as a simple back projection method or a filtered back projection method.

However, with the tomosynthesis imaging, angles at which the radiation can be applied to the subject are limited, and, in the case where the projection images are stacked one on the other using a back projection method, for example, to reconstruct a tomographic image, the tomographic image may include artifacts which are virtual images of structures in an area of the tomographic image where the structures in the subject are not actually present. More specifically, the back projection may introduce artifacts of structures into an area of the tomographic image of a slice plane where the structures are not actually present, i.e., which slice plane is different from a slice plane where the structures are present. When such artifacts are too visible, it is difficult to see a structure, such as a lesion, which is necessary for diagnosis.

During the tomosynthesis imaging, the radiation is applied to the subject a plurality of times, and each time a radiation dose as low as possible is used to reduce the radiation exposure of the subject. However, a low radiation dose results in more quantum noise of radiation in the projection images obtained by the imaging, which in turn results in more visible noise in the reconstructed tomographic image.

Various techniques for reducing such artifacts or noise have been proposed. For example, Japanese Unexamined Patent Publication No. 2013-000261 (hereinafter, Patent Document 1) has proposed a technique which involves: calculating a similarity between each pixel of a reference projection image which is one of projection images and the corresponding pixel of each of the other projection images, which pixels are cumulatively added on the same position on a tomographic image; calculating a weighting factor for each pixel of the projection images such that the weighting factor is larger when the similarity is higher; and reconstructing a tomographic image by performing cumulative addition of products calculated by multiplying each pixel value of each projection image with the corresponding weighting factor.

Besides the above-described technique, techniques called an algebraic reconstruction method or an iterative approximation reconstruction method have also been proposed. These techniques calculate tomographic images such that images formed by projecting the reconstructed tomographic images agree with the actually taken projection images. These techniques allow incorporating various mathematical models in the reconstruction, thereby allowing taking artifact correction, noise reduction, etc., into account to generate tomographic images with suppressed artifacts and reduced noise.

Further, a technique for reducing artifacts while reducing the calculation time has been proposed, which involves: generating a plurality of bandlimited images with different frequency response characteristics from projection images; performing nonlinear transformation on the bandlimited images such that portions that exceed a predetermined value of the bandlimited images become small; adding up the bandlimited images after the nonlinear transformation to generate a plurality of transformed images; and reconstructing a tomographic image from the transformed images (see Japanese Unexamined Patent Publication No. 2013-031641, hereinafter, Patent Document 2).

SUMMARY

When the tomosynthesis imaging is performed, the amount of radiation reaching the radiation detector varies between when the radiation orthogonally enters the radiation detector and when the radiation obliquely enters the radiation detector, and the image quality of the projection images varies depending on the radiation source position with which each projection image is taken. Specifically, comparing a projection image that is obtained when the radiation orthogonally enters the radiation detector with a projection image that is obtained when the radiation obliquely enters the radiation detector, the latter has a lower density and thus is whiter due to smaller amounts of radiation reaching the radiation detector. This results in discrepancy in density between the projection images. In particular, when the radiation obliquely enters the radiation detector, the amounts of radiation reaching the radiation detector vary depending on the position on the radiation detector, resulting in density irregularity on a single projection image. When there are such discrepancy in density and density irregularity based on the different amounts of radiation reaching the radiation detector, it is difficult to accurately calculate the similarity, in particular, with the technique taught in Patent Document 1.

Further, considering the reduction of artifacts of small structures included in the subject, such as calcification in the breast, if there is a large structure at a position other than the slice plane in which small structures are present, it is difficult to accurately calculate the similarity between images of the small structures contained in the projection images due to the influence of the large structure.

For example, consider a case where the radiation is applied to a subject containing a small structure 50 and a large structure 51 from three radiation source positions S1 to S3, as shown in FIG. 24. When the radiation is applied from the radiation source position S1 or S2, the path of radiation transmitted through the small structure 50 does not include the large structure 51, and the small structure 50 captured in each of projection images G1 and G2 is clearly visible without being obstructed by other tissues. On the other hand, when the radiation is applied from the radiation source position S3, the radiation is transmitted through both the small structure 50 and the large structure 51, and the resulting projection image G3 contains the small structure 50 and the large structure 51 overlapped with one another, making the small structure 50 not clearly visible. This hinders accurately calculating the similarity between small structures captured in the projection images, and hinders sufficient improvement of the image quality of the resulting tomographic image.

In view of the above-described circumstances, the present disclosure is directed to improve the image quality of a tomographic image generated from a plurality of projection images obtained by imaging, such as tomosynthesis imaging, with different radiation source positions.

An aspect of a tomographic image generation device according to the disclosure comprises:

an image obtaining unit for obtaining a plurality of projection images corresponding to different radiation source positions, the projection images being taken by moving a radiation source relative to a detecting unit and applying radiation to a subject from the different radiation source positions to which the radiation source is moved;

a frequency decomposition unit for performing frequency decomposition on each of the projection images to obtain a plurality of band projection images representing frequency components for individual frequency bands for each of the projection images;

a reconstruction unit for reconstructing the band projection images for the individual frequency bands to generate band tomographic images of the subject; and a frequency synthesis unit for performing frequency synthesis on the band tomographic images to generate a tomographic image of the subject.

The description "moving a radiation source relative to a detecting unit" as used herein encompasses cases where only the radiation source is moved, only the detecting unit is moved, and both the radiation source and the detecting unit are moved.

In the tomographic image generation device according to the disclosure, the frequency decomposition unit may perform frequency decomposition on each of the projection images with respect to a specific direction on the projection image.

In this case, the specific direction may be a direction in which the radiation source is moved relative to the detection unit.

The tomographic image generation device according to the disclosure may further comprise an emphasis level changing unit for changing emphasis levels for the band tomographic images for desired frequency bands, wherein the frequency synthesis unit performs frequency synthesis on the band tomographic images for the individual frequency bands including the band tomographic images with the changed emphasis levels to generate the tomographic image.

The description "changing emphasis levels" includes both of making the emphasis levels for the desired band tomographic images higher than the emphasis levels for the band tomographic images other than those for the desired frequency bands to increase the pixel values of the desired band tomographic images, and making the emphasis levels for the desired band tomographic images lower than the emphasis levels for the band tomographic images other than those for the desired frequency bands to decrease the pixel values of the desired band tomographic images. Further, the emphasis levels may be changed depending on the frequency band.

In the tomographic image generation device according to the disclosure, the reconstruction unit may comprise:

a pixel value projecting unit for projecting pixel values of the band projection images onto coordinate positions on a desired slice plane of the subject based on a positional relationship between the radiation source position during imaging corresponding to each of the band projection images and the detecting unit, while preserving the pixel values of the band projection images; and a pixel value calculating unit for calculating a pixel value at each coordinate position of interest on the slice plane based on the pixel values of the band projection images projected in a predetermined range relative to the coordinate position of interest on the slice plane to thereby generate the band tomographic images of the slice plane.

It should be noted that each of the band projection images and the band tomographic images is formed by a plurality of pixels which are two-dimensionally and discretely arranged at a given sampling interval, where the pixels are located at grid points corresponding to the given sampling interval. The "pixel positions" as used herein refers to positions corresponding to the grid points on which pixel values forming an image are located on each of the band projection images and the band tomographic images. On the other hand, the "coordinate positions" as used herein includes the grid points on which pixels forming an image are located, i.e., the pixel positions, and positions between the grid points, i.e., positions where pixel values forming the image are not located. That is, the coordinate positions include not only the pixel positions but also positions between the pixel positions.

The band projection images to be projected may be all the band projection images obtained or two or more band projection images of the band projection images obtained.

The "desired slice plane" as used herein refers to a slice plane of the subject for which the tomographic image is generated.

The description "while preserving the pixel values of the band projection images" as used herein refers to that the pixel values of the band projection images are not changed. It should be noted that, in the disclosure, the pixel value at a pixel position of a band projection image may not be able to be projected on a coordinate position on the slice plane. That is, depending on the positional relationship between the radiation source position and the detecting unit, a pixel value of the band projection image corresponding to a coordinate position on the slice plane may not be at a pixel position of the band projection image, but at a coordinate position between pixel positions. In such a case, the pixel value at the coordinate position on the band projection image to be projected on the coordinate position on the slice plane can be calculated by interpolation using pixel values at pixel positions around the coordinate position, for example. In this case, the pixel value calculated by interpolation is also a pixel value of the band projection image, and the pixel value of the band projection image calculated by interpolation is projected on the corresponding coordinate position on the slice plane while being preserved.

The "coordinate position of interest on the slice plane" as used herein refers to a coordinate position for which the pixel value is calculated to generate the band tomographic images of the slice plane. The band tomographic images of the slice plane can be generated by calculating the pixel value at the coordinate position of interest with sequentially changing the coordinate position of interest on the slice plane.

The "predetermined range relative to the coordinate position of interest" as used herein refers to a range of a predetermined number of coordinate positions or pixel positions around and including the pixel position of interest. For example, a range of 3×3 coordinate positions or pixel positions with the pixel position of interest being the center, or a range of 5×5 coordinate positions or pixel positions with the pixel position of interest being the center may be set as the predetermined range relative to the coordinate position of interest. It should be noted that the size of the predetermined range may be fixed or may be changed arbitrarily according to input by the operator.

In the tomographic image generation device according to the disclosure, the pixel value projecting unit may project, for each of the different radiation source positions, pixel values at coordinate positions on the corresponding band projection image intersecting with straight lines that connect the radiation source position and individual pixel positions on the slice plane as pixel values at the pixel positions on the slice plane on the straight lines.

In the tomographic image generation device according to the disclosure, the pixel value projecting unit may project, for each of the different radiation source positions, pixel values at pixel positions on the corresponding band projection image on straight lines that connect the radiation source position and the individual pixel positions on the band projection image as pixel values at coordinate positions on the slice plane intersecting with the straight lines.

In this case, a spacing between coordinate positions on the slice plane may be smaller than a spacing between pixel positions on the slice plane.

In the tomographic image generation device according to the disclosure, the pixel value calculating unit may calculate the pixel value at the coordinate position of interest by performing regression analysis on the pixel values of the band projection images projected on the slice plane.

The "regression analysis" is a statistical technique for analyzing a multivariate relationship. It is assumed here that observed values observed at observation points include noise added to the true values. The regression analysis is a technique to solve an inverse problem to find the true value at every observation point by regression using a least squares method, a moving average method, a kernel function, etc. In the disclosure, the pixel value at the coordinate position of interest is calculated with assuming that each coordinate position on the slice plane with the pixel values of the projection images projected thereon is the observation point, each pixel value at the observation point is the observed value, and the pixel value at the coordinate position of interest is the true value.

In the tomographic image generation device according to the disclosure, the pixel value calculating unit may calculate pixel values at pixel positions on the slice plane by performing the regression analysis to generate a regression surface that represents each band tomographic image of the slice plane, and sampling the regression surface at a desired sampling interval, to thereby generate each band tomographic image.

In this case, the sampling interval may be different from a sampling interval of the band projection images.

By changing the sampling interval of the regression surface, the resolution of the band tomographic images can be changed. For example, a smaller sampling interval results in a higher resolution of the band tomographic images. The "desired sampling interval" as used herein refers to a spacing between pixels with which the band tomographic images having a necessary resolution are obtained. It should be noted that the desired sampling interval may be fixed or may be changed arbitrarily according to input by the operator.

The description "different from a sampling interval of the band projection images" as used herein encompasses both the cases where the sampling interval of the regression surface is greater than the sampling interval of the band projection images, and where the sampling interval of the regression surface is smaller than the sampling interval of the band projection images. If the sampling interval of the regression surface is greater than the sampling interval of the band projection images, the resolution of the generated band tomographic image is lower than the resolution of the band projection images. In contrast, if the sampling interval of the regression surface is smaller than the sampling interval of the band projection images, the resolution of the generated band tomographic image is higher than the resolution of the band projection images.

In the tomographic image generation device according to the disclosure, if an instruction to change the size of an area of interest in the tomographic image being displayed is received, the pixel value calculating unit may generate a tomographic image of the area of interest with changing the sampling interval of an area of each regression surface corresponding to the area of interest according to the instruction to change.

In the tomographic image generation device according to the disclosure, the pixel value calculating unit may change sharpness of the pixel value at the coordinate position of interest when the regression analysis is performed.

The description "change sharpness" as used herein encompasses emphasizing the sharpness such that an edge included in the generated tomographic image is emphasized, and reducing the sharpness such that the generated tomographic image is smoothed to reduce noise.

In this case, the pixel value calculating unit may change a level of change of the sharpness depending on information of at least one of imaging conditions during the imaging and a structure of the subject included in the band projection images.

When the projection images are taken, a smaller amount of radiation that reaches the detector results in more noise in the projection images. The amount of noise in the band projection images and the sharpness of the obtained images also vary depending on the radiation quality of the x-ray, i.e., whether the x-ray is a high voltage x-ray or a low voltage x-ray, the type of material forming the detecting unit, or the presence or absence of a grid used to remove scattered rays during imaging. The "imaging conditions" as used herein refer to various conditions that influence the amount of noise and the sharpness of the band projection images, and examples thereof may include the amount of radiation that reaches the detector during imaging, the type of the detecting unit, or the presence or absence of the grid. The "structure of the subject" as used herein refers to a structure, such as edges, included in the subject.

A preferred sharpness of the band tomographic images depends on the preference of the user, such as a doctor, who observes the generated image. Therefore the sharpness may be changeable according to the preference of the user.

In the tomographic image generation device according to the disclosure, the pixel value calculating unit may calculate the pixel value at the coordinate position of interest with removing an outlier pixel value among the pixel values of the band projection images projected in the predetermined range relative to the coordinate position of interest or assigning the outlier pixel value with a small weight.

The "outlier" as used herein refers to a pixel value that is largely different from the other pixel values among the pixel values of the projection images projected in the predetermined range relative to the coordinate position of interest. The expression "largely different" as used herein means that a difference between the value of the outlier and an average value of the pixel values projected in the predetermined range relative to the coordinate position of interest, for example, exceeds a predetermined threshold value.

In the tomographic image generation device according to the disclosure, the pixel value projecting unit may correct, based on a positional relationship between a given radiation source position and each coordinate position of interest on each of the band projection images for the individual frequency bands corresponding to the given radiation source position, a coordinate position on the slice plane on which a pixel value at the coordinate position of interest on the band projection image is projected such that two-dimensional coordinates of the coordinate position of interest on the band projection image agrees with two-dimensional coordinates of the coordinate position on the slice plane on which the pixel value at the coordinate position of interest on the band projection image is projected, and may project the pixel values of the band projection images onto the corrected coordinate positions on the slice plane.

In this case, the image obtaining unit may obtain a radiographic image of the subject taken by applying the radiation to the subject from the given radiation source position, the pixel value calculating unit may generate the band tomographic images by calculating the pixel value at each coordinate position of interest on the slice plane with the pixel values of the projection images being projected on the corrected coordinate positions, the frequency synthesis unit may perform the frequency synthesis on the generated band tomographic images to generate the tomographic image, and the tomographic image generation device may further comprise a display unit for displaying the radiographic image and the tomographic image.

The "radiographic image of the subject" as used herein refers to an image including a transmission image of a structure included in the subject, which image is obtained by imaging the subject under imaging conditions for obtaining a transmission image of the subject with the radiation source position being fixed at the given radiation source position.

In the tomographic image generation device according to the disclosure, the pixel value calculating unit may calculate a weighting factor based on a difference between a pixel value at the coordinate position of interest and a pixel value at a coordinate position on each band projection image corresponding to the coordinate position of interest, and may calculate a pixel value at the coordinate position of interest again based on the pixel values of the band projection images and the weighting factors to calculate a new pixel value at the coordinate position of interest.

In this case, the pixel value calculating unit may iterate calculating a new weighting factor using the new pixel value at the coordinate position of interest, and calculating a new pixel value at the coordinate position of interest again based on the pixel values of the projection images and the new weighting factors.

As the "weighting factor", for example, such a factor that the value of which decreases as the difference between the pixel value at the coordinate position of interest and the pixel value at a coordinate position on the band projection image corresponding to the coordinate position of interest increases.

The number of iterations of the calculation of a new weighting factor using the new pixel value at the coordinate position of interest and the calculation of a new pixel value at the coordinate position of interest based on the pixel values of the band projection images and the new weighting factors may be determined in advance, or the calculations may be iterated until a specific convergence condition is met, such that the difference between the new pixel value at the coordinate position of interest and the pixel value at a coordinate position on the band projection image corresponding to the coordinate position of interest becomes smaller than a predetermined threshold value.

In the tomographic image generation device according to the disclosure, the frequency decomposition unit, the reconstruction unit, and the frequency synthesis unit may generate tomographic images for a plurality of slice planes of the subject, and the tomographic image generation device may further comprise a pseudo image generation unit for generating a pseudo image from the tomographic images.

The "pseudo image" as used herein refers to a pseudo image that appears as an image of a type that is different from the tomographic image. An example thereof is an addition tomographic image that is generated by simply adding up pixel values at corresponding pixel positions of the tomographic images so that it appears as a transmission image obtained by ordinary radiographic imaging. Besides the addition tomographic image, a maximum projection image that appears as a three-dimensional image obtained by an MIP (Maximum Intensity Projection) method that extracts maximum values from corresponding pixel positions of the tomographic images, and a minimum projection image that appears as a three-dimensional image obtained by a minIP (Minimum Intensity Projection) method that extracts minimum values from corresponding pixel positions of the tomographic images can be used as the pseudo image.

An aspect of a tomographic image generation method according to the disclosure comprises the steps of:
obtaining a plurality of projection images corresponding to different radiation source positions, the projection images being taken by moving a radiation source relative to a detecting unit and applying radiation to a subject from the different radiation source positions to which the radiation source is moved;
performing frequency decomposition on each of the projection images to obtain a plurality of band projection images representing frequency components for individual frequency bands for each of the projection images;
reconstructing the band projection images for the individual frequency bands to generate band tomographic images of the subject; and
performing frequency synthesis on the band tomographic images to generate a tomographic image of the subject.

The tomographic image generation method according to the disclosure may be provided in the form of a program for causing a computer to execute the tomographic image generation method.

According to the disclosure, frequency decomposition is performed on each of the projection images to obtain a plurality of band projection images representing frequency components for individual frequency bands for each of the projection images. Then, the band projection images are reconstructed for the individual frequency bands to generate band tomographic images of the subject. Further, frequency synthesis is performed on the band tomographic images for the individual frequency bands to generate a tomographic image of the subject. Note that small structures contained in the subject are contained in band projection images for relatively high frequency bands, and large structures as well as density irregularity in an image and discrepancy in density between images are contained in band projection images for relatively low frequency bands. According to the disclosure, the band projection images are reconstructed for the individual frequency bands. This allows, with respect to the relatively high frequency bands, projecting small structures contained in the subject to be projected to generate the band tomographic images without being influenced by large structures as well as the density irregularity and the discrepancy in density. Further, artifacts can be removed for each frequency band, and this allows reducing artifacts due to differences of the sizes of structures contained in the subject as well as the density irregularity and the discrepancy in density. Thus, according to the disclosure, tomographic images with higher image quality can be generated.

BRIEF DESCRIPTION OF THE DRAWINGS

FIG. 1 is a diagram illustrating the schematic configuration of a radiographic imaging apparatus to which a tomographic image generation device according to a first embodiment of the disclosure is applied, FIG. 2 is a diagram illustrating the radiographic imaging apparatus viewed from the direction of arrow A in FIG. 1, FIG. 3 is a diagram illustrating the schematic configuration of the tomographic image generation device of the first embodiment implemented by installing a tomographic image generation program on a computer, FIG. 4 is a diagram for explaining how projection images are obtained, FIG. 13 is a flow chart illustrating a process performed in the first embodiment, FIG. 14 is a diagram for explaining how pixel values are projected in a second embodiment, FIG. 19 is a diagram illustrating the schematic configuration of a tomographic image generation device of a fifth embodiment implemented by installing a tomographic image generation program on a computer, FIG. 20 shows a state where an enlarged image of an area of interest is displayed on a display unit.

DETAILED DESCRIPTION OF THE PREFERRED EMBODIMENTS

Figure 5:
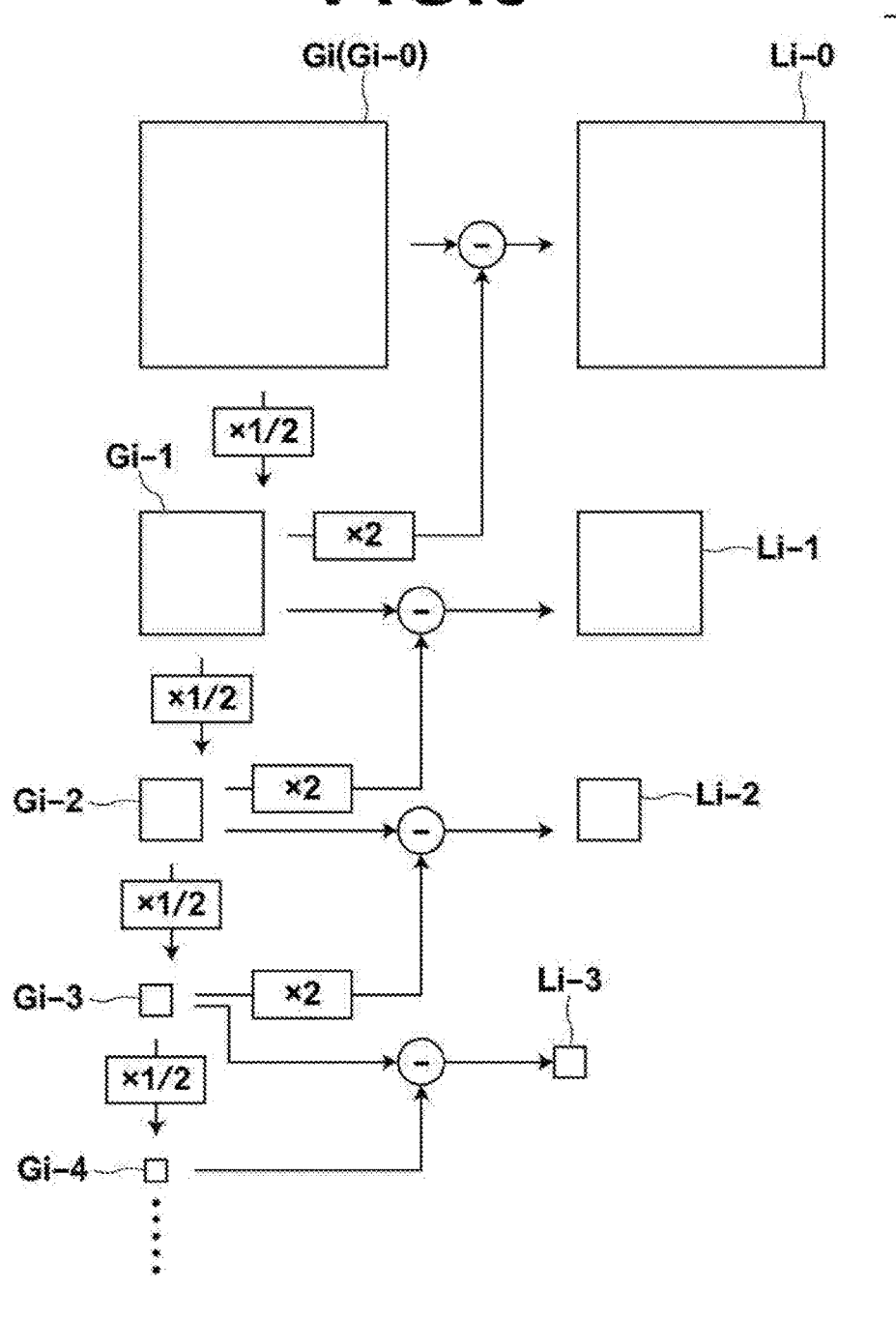
FIG. 5 is a diagram for explaining frequency decomposition in the first embodiment.

Hereinafter, embodiments of the present disclosure will be described with reference to the drawings. FIG. 1 is a diagram illustrating the schematic configuration of a radiographic imaging apparatus to which a tomographic image generation device according to a first embodiment of the disclosure is applied, and FIG. 2 is a diagram illustrating the radiographic imaging apparatus viewed from the direction of arrow A in FIG. 1. The radiographic imaging apparatus 1 is a mammographic apparatus that images a breast M (which may hereinafter also be referred to as "subject M") with different radiation source positions, which correspond to different imaging directions, to obtain a plurality of radiographic images, i.e., projection images, to generate a tomographic image of the breast by performing tomosynthesis imaging. As shown in FIG. 1, the radiographic imaging apparatus 1 includes an imaging unit 10, a computer 2 connected to the imaging unit 10, and a display unit 3 and an input unit 4 connected to the computer 2.

The imaging unit 10 includes an arm 12, which is coupled to a base (not shown) via a rotatable shaft 11. An imaging table 13 is attached to one end of the arm 12, and a radiation applying unit 14 is attached to the other end of the arm 12 so as to face the imaging table 13. The arm 12 is configured such that only the end to which the radiation applying unit 14 is attached can be rotated, thereby allowing only the radiation applying unit 14 to be rotated while the imaging table 13 is fixed. Rotation of the arm 12 is controlled by the computer 2.

The imaging table 13 includes therein a radiation detector 15 (detecting unit), such as a flat panel detector. The imaging table 13 also includes therein a circuit board, etc., which includes a charge amplifier for converting an electric charge signal read out from the radiation detector 15 into a voltage signal, a correlated double sampling circuit for sampling the voltage signal outputted from the charge amplifier, an AD converter for converting the voltage signal into a digital signal, etc.

The radiation detector 15 is of a type that is repeatedly usable to record and read out a radiographic image on and from it. The radiation detector 15 may be a so-called direct-type radiation detector, which directly receives the radiation and generates electric charges, or may be a so-called indirect-type radiation detector, which once converts the radiation into visible light, and then converts the visible light into electric charge signals. As the reading system to read out the radiographic image signal, it is desirable to use a so-called TFT reading system, which reads out the radiographic image signal with turning on and off TFT (thin film transistor) switches, or a so-called optical reading system, which reads out the radiographic image signal by applying reading light. However, this is not intended to limit the invention and any other reading system may be used.

The radiation applying unit 14 contains therein an x-ray source 16, which is a radiation source. Timing of application of x-rays from the x-ray source 16 and x-ray generation conditions for the x-ray source 16, i.e., imaging conditions including tube current, time, tube current time product, etc., are controlled by the computer 2.

To the arm 12, a compression paddle 17 disposed above the imaging table 13 for compressing the breast M, a support 18 for supporting the compression paddle 17, and a moving mechanism 19 for moving the support 18 in the vertical direction, as shown in FIGS. 1 and 2, are attached.

The display unit 3 is a display device, such as a CRT or a liquid crystal monitor. The display unit 3 displays projection images which are obtained as described later, a generated tomographic image, and messages necessary for operation, etc. The display unit 3 may include a built-in speaker for outputting sound.

The input unit 4 is formed by a keyboard, a mouse, and/or a touch-panel input device. The input unit 4 receives operation by the operator of the radiographic imaging apparatus 1. The input unit 4 also receives input of various information, such as imaging conditions, necessary for performing tomosynthesis imaging, and instructions to modify the information. In this embodiment, the individual units of the radiographic imaging apparatus 1 operate according to the information inputted by the operator via the input unit 4.

A tomographic image generation program is installed on the computer 2. In this embodiment, the computer may be a work station or a personal computer which is directly operated by the operator, or may be a server computer connected to the work station or the personal computer via a network. The tomographic image generation program is distributed with being recorded on a recording medium, such as a DVD (Digital Versatile Disc) or a CD-ROM (Compact Disc Read Only Memory), and is installed on the computer from the recording medium. Alternatively, the tomographic image generation program is stored on a storage device of a server computer connected to a network or a network storage such that it is externally accessible, and is download and installed on the computer in response to a request.

FIG. 3 is a diagram illustrating the schematic configuration of the tomographic image generation device implemented by installing the tomographic image generation program on the computer 2. As shown in FIG. 3, the tomographic image generation device includes a CPU (Central Processing Unit) 21, a memory 22, and a storage 23, as the configuration of a standard computer.

The storage 23 is formed by a storage device, such as a hard disk or SSD (solid state drive). The storage 23 stores various information including programs for driving the individual units of the radiographic imaging apparatus 1, and the tomographic image generation program. The storage 23 also stores projection images obtained by tomosynthesis imaging, and a tomographic image which is generated as described later.

The memory 22 temporarily stores the programs stored in the storage 23 for the CPU 21 to execute various operations. The tomographic image generation program defines, as the operations to be executed by the CPU 21: an image obtaining operation for causing the radiographic imaging apparatus 1 to perform tomosynthesis imaging to obtain a plurality of projection images of the breast M; a frequency decomposition operation for performing frequency decomposition on each of the projection images to obtain a plurality of band projection images representing frequency components for individual frequency bands for each of the projection images; a reconstruction operation for reconstructing the band projection images for the individual frequency bands to generate band tomographic images of the subject; and a frequency synthesis operation for performing frequency synthesis on the band tomographic images to generate a tomographic image of the subject.

Further, in this embodiment, the reconstruction operation defines a pixel value projecting operation for projecting pixel values of the band projection images onto coordinate positions on a desired slice plane of the breast M, which is the subject, based on a positional relationship between the position of the x-ray source 16 during imaging corresponding to each of the band projection images and the radiation detector 15, while preserving the pixel values of the band projection images for the individual frequency bands; and a pixel value calculating operation for calculating a pixel value at each coordinate position of interest on the desired slice plane based on the pixel values of the band projection images projected in a predetermined range relative to the coordinate position of interest on the desired slice plane to thereby generate the band tomographic images.

When the CPU 21 executes the above-described operations according to the tomographic image generation program, the computer 2 functions as an image obtaining unit 31, a frequency decomposition unit 32, a reconstruction unit 33, and a frequency synthesis unit 34. With respect to the reconstruction unit 33, the computer 2 functions as a pixel value projection unit 35 and a pixel value calculation unit 36. It should be noted that the computer 2 may include processors for executing the image obtaining operation, the frequency decomposition operation, the reconstruction operation, and the frequency synthesis operation, as well as the pixel value projection operation and the pixel value calculation operation, respectively.

The image obtaining unit 31 causes the arm 12 to rotate about the rotatable shaft 11 to move the x-ray source 16, applies x-rays to the breast M, which is the subject, from different radiation source positions to which the x-ray source 16 is moved, and detects the x-rays transmitted through the breast M with the radiation detector 15 to obtain a plurality of projection images Gi (i=1 to n, where n is the number of radiation source positions) corresponding to the different radiation source positions. FIG. 4 is a diagram for explaining how the projection images Gi are obtained. As shown in FIG. 4, the x-ray source 16 is moved to each of radiation source positions S1, S2, . . . , Sn, and the x-ray source 16 is activated at each radiation source position to apply x-rays to the breast M. Then, the x-rays transmitted through the breast M are detected with the radiation detector 15 to obtain projection images G1, G2, . . . ,Gn corresponding to the radiation source positions S1 to Sn. The obtained projection images Gi are stored in the storage 23. It should be noted that the projection images Gi may be obtained and stored in the storage 23 under the control of a program separate from the tomographic image generation program. In this case, the image obtaining unit 31 reads out the projection images Gi, which are stored in the storage 23, from the storage 23 for the frequency decomposition operation, the reconstruction operation, and the frequency synthesis operation.

In this embodiment, all the projection images Gi stored in the storage 23 may be read out to be used for the frequency decomposition operation, the reconstruction operation, and the frequency synthesis operation, or a predetermined number of (two or more) projection images Gi among the projection images Gi stored in the storage 23 may be read out to be used for the frequency decomposition operation, the reconstruction operation, and the frequency synthesis operation.

The frequency decomposition unit 32 performs frequency decomposition on each of the projection images Gi to obtain a plurality of band projection images representing frequency components for individual frequency bands for each of the projection images Gi. FIG. 5 is a diagram for explaining the frequency decomposition performed by the frequency decomposition unit 32. First, the frequency decomposition unit 32 filters a projection image Gi for a given frequency band with a Gaussian filter with σ=1, for example, to reduce the projection image Gi by half to generate a reduced image Gi-1 of Gaussian components. The reduced image Gi-1 corresponds to the projection image Gi reduced by half. It should be noted that, in the following description, the projection image Gi may be referred to as a projection image Gi-0, for convenience. Then, the frequency decomposition unit 42 performs interpolation, such as third-order B-spline interpolation, to enlarge the reduced image Gi-1 twice such that the size of the reduced image Gi-1 becomes the same as the size of the projection image Gi-0, and subtracts the thus enlarged reduced image Gi-1 from the projection image Gi-0 to generate a band projection image Li-0 of Laplacian components for the highest frequency band. It should be noted that, in this embodiment, the highest frequency band may be referred to as the 0th frequency band, for convenience.

Subsequently, the frequency decomposition unit 42 filters the reduced image Gi-1 with a Gaussian filter with σ=1 to reduce the reduced image Gi-1 by half to generate a reduced image Gi-2, and enlarges the reduced image Gi-2 twice such that the size of the reduced image Gi-2 becomes the same as the size of the reduced image Gi-1. Then, the frequency decomposition unit 42 subtracts the thus enlarged reduced image Gi-2 from the reduced image Gi-1 to generate a band projection image Li-1 for the 1st frequency band. The above-described operations are repeated until band projection images for desired frequency bands are generated, to thereby generate band projection images Li-k (where k=0 to a, where a is the number of bands) for a plurality of frequency bands. In this embodiment, the above-described operations are repeated until a band projection image Li-10 for the 10th frequency band is obtained, where a=10, for example.

The signal value of each pixel of the reduced images represents the density at the pixel, and the signal value of each pixel of the band projection images Li-k represents the magnitude of the frequency component for the corresponding frequency band at the pixel. It should be noted that the band projection images Li-k for different frequency bands may be generated by using a different multi-resolution conversion technique, such as wavelet transform.

Figure 6:
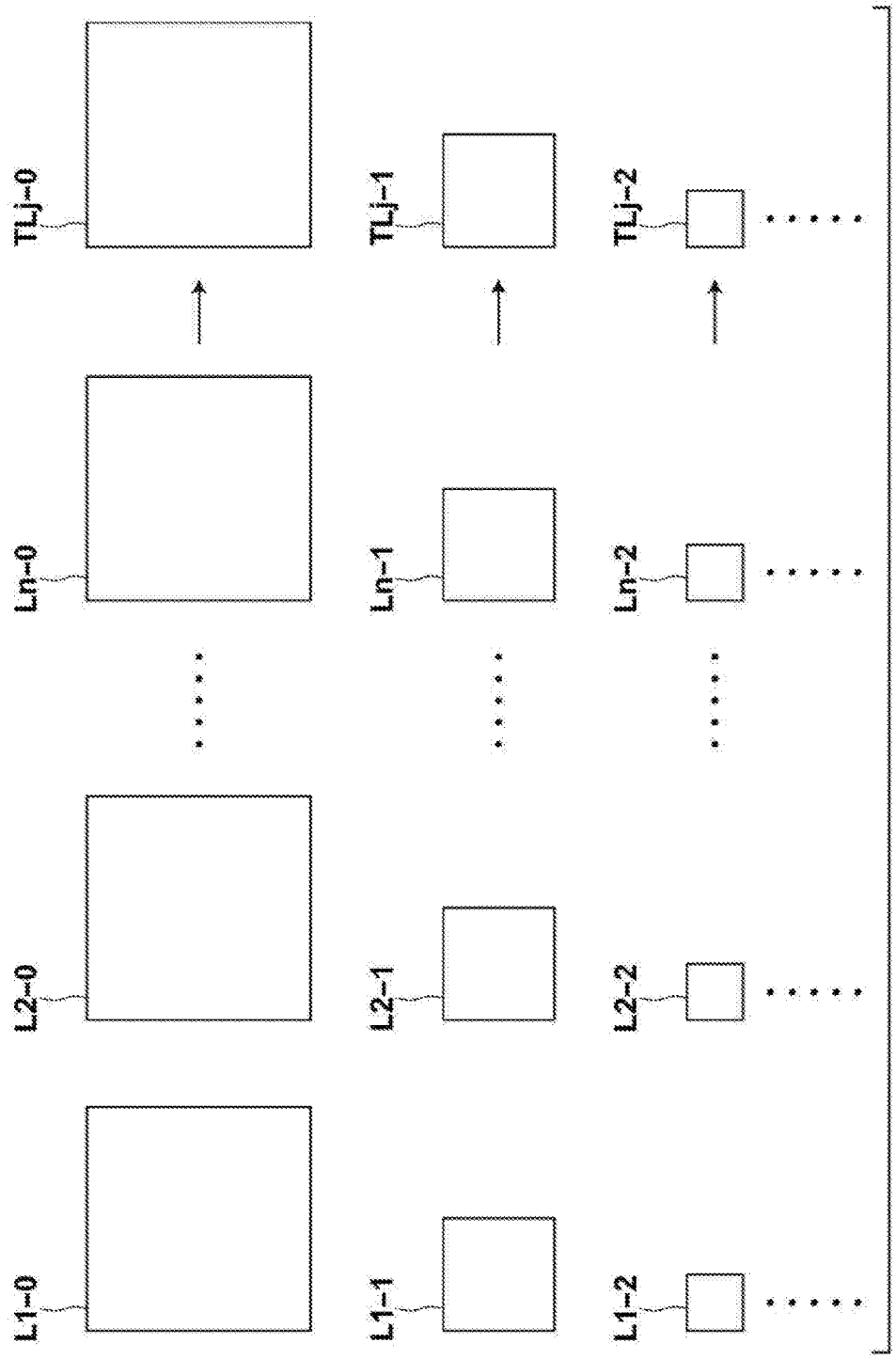
FIG. 6 is a diagram for explaining a reconstruction operation in the first embodiment.

FIG. 6 is a diagram for explaining the reconstruction operation. As shown in FIG. 6, the reconstruction unit 33 reconstructs the band projection images Li-k for the individual frequency bands to generate band tomographic images TLj-k for the individual frequency bands of the subject. In this embodiment, the pixel value projection unit 35 and the pixel value calculation unit 36 performs the reconstruction operation.

Figure 7:
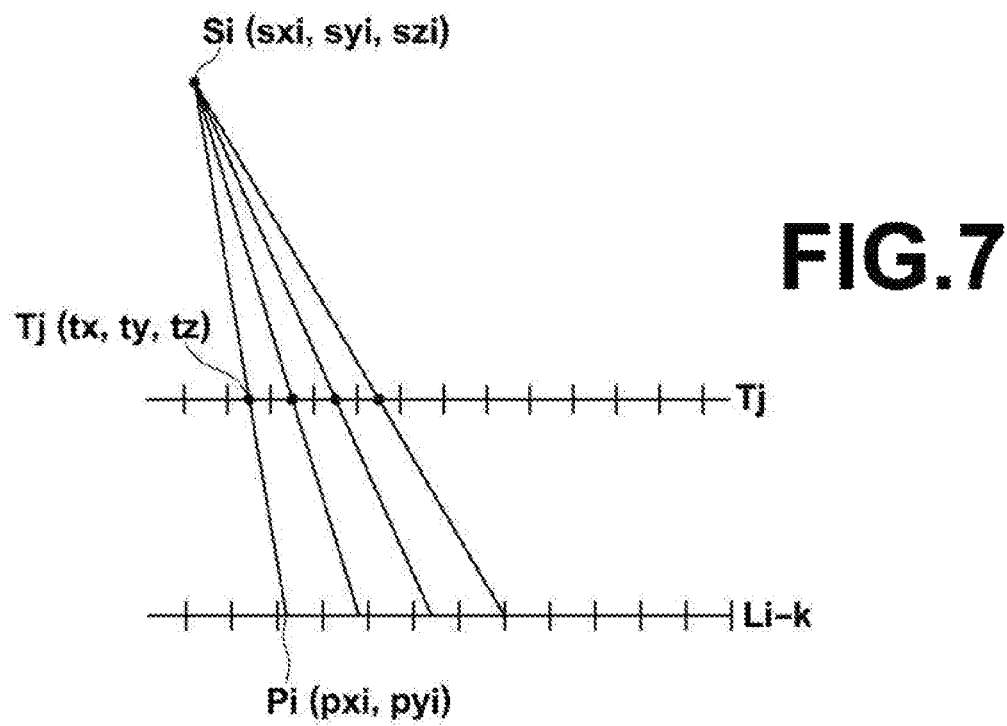
FIG. 7 is a diagram for explaining how pixel values are projected in the first embodiment.

The pixel value projection unit 35 projects pixel values of the band projection images Li-k for the individual frequency bands generated by the frequency decomposition unit 32 on coordinate positions on a desired slice plane of the breast M, while preserving the pixel values of the band projection images Li-k for the individual frequency bands. FIG. 7 is a diagram for explaining how the pixel values are projected in the first embodiment. It should be noted that FIG. 7 explains a case where a band projection image Li-k obtained from a projection image Gi which is obtained with a radiation source position Si is projected on a desired slice plane Tj (j=1 to m, where m is the number of slice planes) of the breast M.

The band projection images Li-k and the band tomographic images TLj-k of the slice plane Tj, which are generated as described later, are formed by a plurality of pixels which are two-dimensionally and discretely arranged at a given sampling interval, where the pixels are located at grid points corresponding to the given sampling interval. In FIG. 7 and FIG. 14, which will be described later, the short line segments orthogonally crossing the band projection image Li-k and the slice plane Tj represent boundary positions between the pixels. In FIG. 7 and FIG. 14, which will be described later, each center position between the pixel boundary positions is a pixel position, which is the grid point. As shown in FIG. 7, in the first embodiment, pixel values at positions on the band projection image Li-k intersecting with the straight lines that connect the radiation source position Si and the individual pixel positions on the slice plane Tj are projected as pixel values at the pixel positions on the slice plane Tj on the corresponding straight lines.

Assuming that coordinates of the radiation source position Si are (sxi, syi, szi), and coordinates of a pixel position on the slice plane Tj are Tj(tx, ty, tz), coordinates (pxi, pyi) of the corresponding coordinate position Pi on the band projection image Li-k are expressed by the equations (1) below. In this embodiment, the z-axis is set in the direction perpendicular to the detection surface of the radiation detector 15, the y-axis is set in the direction along the detection surface of the radiation detector 15 parallel to the direction in which the x-ray source 16 is moved, and the x-axis is set in the direction orthogonal to the y-axis.

$$pxi=(tx \times szi - sxi \times tz)/(szi-tz),$$

$$pyi=(ty \times szi - syi \times tz)/(szi-tz) \qquad (1).$$

Figure 8:
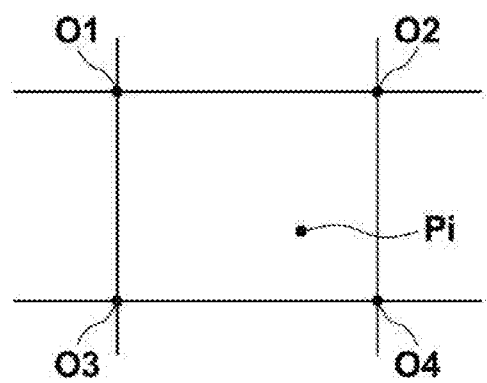
FIG. 8 is a diagram for explaining how a pixel value of a projection image is interpolated.

It should be noted that there are cases where the coordinate position Pi on the band projection image Li-k is not a pixel position on the band projection image Li-k. For example, as shown in FIG. 8, a coordinate position Pi on the band projection image Li-k may be between four pixel positions O1 to O4 on the band projection image Li-k. In this case, interpolation is performed using pixel values at the four pixel positions O1 to O4, which are nearest to the coordinate position Pi of the band projection image Li-k, as shown in FIG. 8, to calculate the pixel value at the coordinate position Pi, and the calculated pixel value is projected on the pixel position Tj(tx, ty, tz) on the slice plane Tj. As the interpolation, any technique, such as linear interpolation where the pixel values at the four pixel positions are weighted depending on the distance between the coordinate position Pi and each of the four pixel positions, non-linear bicubic interpolation using pixel values at more pixel positions around the coordinate position Pi, or B-spline interpolation, may be used. In place of performing the interpolation, the pixel value at the pixel position which is nearest to the coordinate position Pi may be used as the pixel value at the coordinate position Pi.

Figure 9:
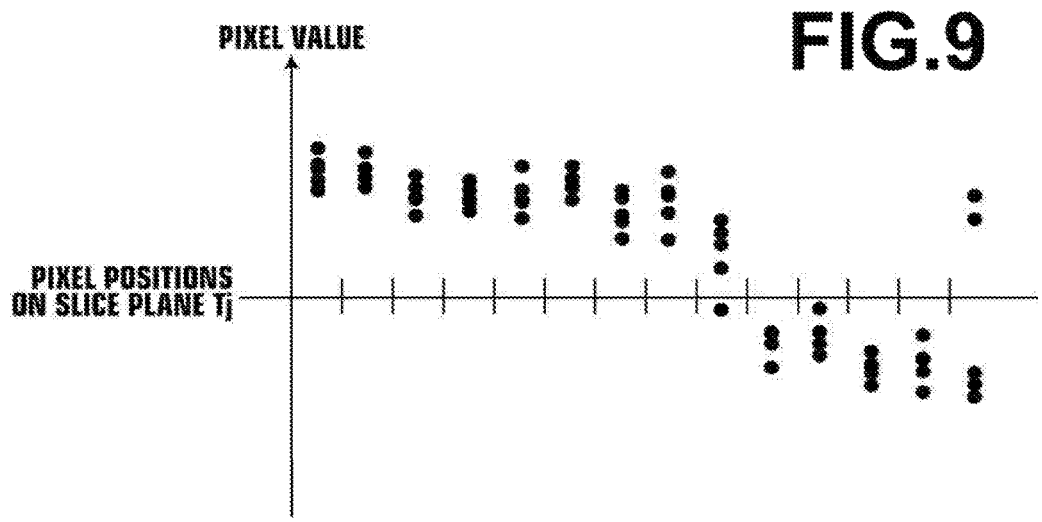
FIG. 9 shows pixel values projected on a slice plane in the first embodiment.

The pixel value projecting unit 32 projects, for each radiation source position Si, the pixel values of the corresponding band projection image Li-k on the slice plane Tj. As a result, n pixel values corresponding to the number of the band projection images Li-k are projected on each pixel position on the slice plane Tj, as shown in FIG. 9. FIG. 9 shows a state where pixel values of five projection images are projected on each pixel position. In FIG. 9, and in FIGS. 10, 11, 15, 22, and 23, which will be described later, the short line segments orthogonally crossing the slice plane Tj represent boundary positions between pixels, and the center positions between the pixel boundary positions are the pixel positions, which are the grid points.

The pixel value calculating unit 36 generates a band tomographic image TLj-k of the slice plane Tj for each frequency band by calculating each pixel value on the slice plane Tj. Specifically, the pixel value at each coordinate position of interest is calculated based on a plurality of pixel values of the band tomographic images TLj-k projected in a predetermined range relative to the coordinate position of interest for which the pixel value is calculated. It should be noted that the coordinate position of interest may be a pixel position on the slice plane Tj. While the pixel values of the band tomographic images TLj-k are projected on the pixel positions on the slice plane Tj in the first embodiment, the pixel value at each coordinate position of interest may be calculated using the pixel values projected on the coordinate position of interest, or without using the pixel values projected on the coordinate position of interest. Now, how the pixel value at each coordinate position of interest is calculated is described.

The pixel values of the band projection images Li-k projected on the slice plane Tj by the pixel value projecting unit 35 tend to be more similar when they are nearer to each other. Therefore the pixel value calculating unit 36 performs an operation to change the sharpness such that the pixel values projected on the slice plane Tj are smoothly continuous. In this embodiment, the pixel values projected on the slice plane Tj are filtered with a smoothing filter. Specifically, pixel values at pixel positions in a predetermined range, such as 3×3 or 5×5, with the coordinate position of interest being the center are filtered with a Gaussian filter, for example. This renders the pixel values of pixels at and around the coordinate position of interest smoothly continuous, thereby suppressing noise, such as quantum noise, which is originally included in the band projection images Li-k, in the pixel values projected on the slice plane Tj.

A value defining the size of the predetermined range may be stored as a fixed value in the storage 23. Further, the value may be changed arbitrarily according to input by the operator via the input unit 4. In this case, the value defining the size of the predetermined range stored in the storage 23 is rewritten according to input by the operator via the input unit 4 and the size of the predetermined range is changed.

The level of smoothness, i.e., the level of noise suppression can be changed by changing the filter size of the Gaussian filter. Specifically, increasing the filter size to increase the range of filtering with the coordinate position of interest being the center allows higher level of noise suppression. It should be noted that lower amounts of x-rays reaching the radiation detector 15 when the projection images Gi are taken result in more noise in the projection images Gi, which in turn results in more noise in the pixel values projected on the slice plane Tj. The amounts of noise in the projection images Gi also vary depending on the radiation quality of the x-rays, i.e., whether the x-rays are high voltage x-rays or low voltage x-rays. The amounts of noise in the projection images Gi also vary depending on the type of the radiation detector 15 used to take the projection images. Further, in some cases, a scattered ray removing grid may be disposed between the radiation detector 15 and the subject M when the projection images Gi are taken in order to prevent influence of scattered rays of the x-rays on the subject M. The amounts of noise in the projection images Gi also vary depending on the type of the scattered ray removing grid, or the presence or absence of the scattered ray removing grid. In this manner, when the amounts of noise contained in the projection images Gi change, the amounts of noise contained in the band projection images Li-k also change.

For this reason, in this embodiment, properties of the smoothing filter are changed based on the imaging conditions, such as the amounts of x-rays reaching the radiation detector 15, the radiation quality of the x-rays, the type of the radiation detector 15, the type of the scattered ray removing grid, and the presence or absence of the scattered ray removing grid. For example, for the imaging conditions which result in more noise in the projection images Gi, the filter size is increased so that higher level of noise suppression is achieved.

When a Gaussian filter is used for the filtering, edges which are structures of the subject M included in a tomographic image which is generated as described later may be blurred. For this reason, the filtering may be performed using a bilateral filter which assigns neighboring pixels around the coordinate position of interest with weights depending on the distance between the pixels, and also assigns the neighboring pixels around the coordinate position of interest with normally distributed weights such that the weight is smaller when the difference between pixel values is greater. Alternatively, the filtering may be achieved using a non-local means filter which performs weighting based on similarity between a neighboring area around the coordinate position of interest on the slice plane Tj and a neighboring area around an arbitrary pixel on the slice plane Tj. This allows suppressing noise while preserving edges, thereby preventing lowering of the sharpness of a tomographic image which is generated as described later.

Further, the pixel values projected on the slice plane Tj may be filtered with a differential filter, for example, to detect an edge, which is the structure of the subject where there is a sudden change in the pixel value that exceeds a predetermined threshold value, and the filter properties may be changed such that the filtering is applied along the direction in which the edge extends, to thereby change the level of sharpness. Still further, the filtering may be performed such that, with respect to pixel values along a boundary of an edge, pixel values at positions beyond the edge are not used. This allows preventing the edge from being smoothed, thereby preventing lowering of the sharpness of the distribution of the pixel values projected on the slice plane Tj while suppressing noise.

In place of or in addition to the smoothing, an operation to emphasize the sharpness may be performed to emphasize edges. In this case, it is preferred to perform the operation to emphasize the sharpness along the direction in which each edge extends.

After the filtering is performed as described above, the pixel value calculating unit 36 performs regression analysis on the pixel values of the band projection images Li-k projected on the slice plane Tj to generate a curved surface, or a regression surface, that represents a band tomographic image TLj-k of the slice plane Tj. In the following description, the regression surface is considered as a regression curve for ease of explanation. The regression analysis is a statistical technique for analyzing a multivariate relationship. It is assumed here that observed values observed at observation points include noise added to the true values. The regression analysis is a technique to solve an inverse problem to find the true value at every observation point by a least squares method, a moving average method, regression using a kernel function, etc. In the first embodiment, a pixel value rm at each coordinate position of interest um is calculated by the regression analysis with assuming that each coordinate position on the slice plane Tj with the pixel values of the band projection images Li-k projected thereon is an observation point uk, each pixel value of the band projection images Li-k projected on the observation point uk is an observed value qk, and the pixel value calculated for the coordinate position of interest um is a true value rm.

In the case where a least squares method is used, it is assumed that the true value follows a function whose distribution is defined by γ parameters a, i.e., r=f(u|a1, a2, ..., aγ). Then, the function f can be determined by finding the parameters a1, a2, ..., aγ which minimize squared errors between the true values and the observed values. Specifically, the pixel value rm at each coordinate position of interest is calculated by determining the parameters of the function f according to the equation (2) below, such that the total sum of errors of the observed values at the observation points is minimized, to generate the regression curve (regression surface). It should be noted that, as shown by the equation (3) below, a weight wk may be set for each observation point uk, and the regression curve (regression surface) may be generated by calculating the pixel value rm at each coordinate position of interest um by a weighted least squares method.

$$r_m = \sum_k \{q_k - f(u_k)\}^2 \quad (2)$$

$$r_m = \sum_k w_k \{q_k - f(u_k)\}^2 \quad (3)$$

In the case where a moving average method is used, the regression surface is generated by calculating the pixel value at each coordinate position of interest by the moving average method. Specifically, considering the regression surface as a regression curve for ease of explanation, for the pixel value at each coordinate position of interest urn, an average value {(qk−1)+qk+(qk+1)}/3 of the pixel values of the band projection images Li-k projected on three coordinate positions adjacent to the coordinate position of interest um, i.e., coordinate positions uk−1, uk, and uk+1, for example, is calculated, and the calculated average value is used as the pixel value at the coordinate position of interest um. It should be noted that a weight may be set for each pixel value. For example, weights may be set such that the weight is smaller as the distance from the coordinate position of interest um is greater.

In the case where regression using a kernel function is used, the regression curve (regression surface) is calculated by determining a kernel function, according to the equation (4) below, for each coordinate position of interest um and the observation points uk on the slice plane Tj on which the pixel values of the projection images are projected. The "argmin" in the equation (4) means that the value of r(um) that minimizes the right side is calculated.

$$r(u_m) = \underset{r(u_m)}{\mathrm{argmin}} \sum_k \{q_k - r(u_m)\}^2 \ K(u_k, u_m, q_k, q_m) \quad (4)$$

The above-described filtering for smoothing can be integrated into the regression analysis. In the case where the least squares method is used, using a low-dimensional function as the function f results in a higher level of smoothing of the generated regression surface. In contrast, using a high-dimensional function as the function f results in a higher level of sharpness of the generated regression surface. In the case where the moving average is used, the level of smoothing can be changed by changing the number of pixels for which the average is calculated, or changing the level of weighting. Namely, increasing the number of pixels for which the average is calculated results in a higher level of smoothing. Also, the level of smoothing may be changed by changing the level of weighting depending on the imaging conditions, as described above.

With the regression technique using a kernel function, the level of smoothing can be changed depending on the design of the kernel function. In particular, the regression technique using a kernel function allows obtaining an effect similar to that of the weighted least squares method and emphasizing edges depending on the design of the kernel function. For example, when the kernel function expressed by the equation (5) below is used, the regression surface is generated such that a pixel value closer to the observed value qk at the observation point uk is calculated when the distance between the coordinate position of interest um and the observation point uk is smaller. This allows obtaining a smoothing effect similar to that obtained by using a Gaussian filter. The "$h_x$" in the equation (5) is a bandwidth parameter.

$$K(u_k, u_m) = \exp\left(\frac{-\|u_k - u_m\|^2}{h_x^2}\right) \quad (5)$$

Figure 10:
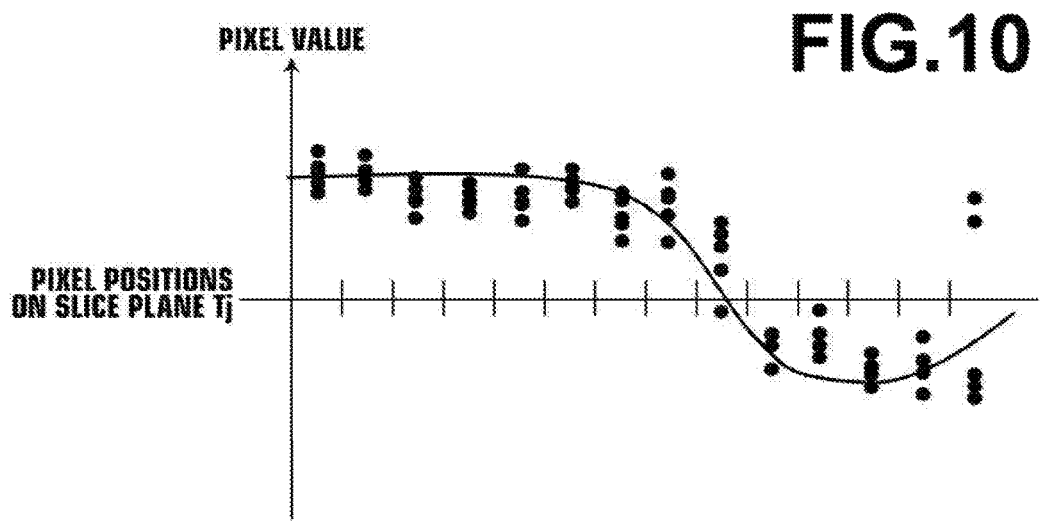
FIG. 10 is a diagram for explaining how a regression curve (regression surface) including outliers is generated.

In FIG. 9, two pixel values among the five pixel values projected on the rightmost pixel position on the slice plane Tj are largely different from the pixel values at the adjacent pixel position. If there are pixel values that are largely different from the pixel values of the adjacent pixels, the value of the generated regression surface at the pixel position which includes the outliers is largely different from the value at the adjacent pixel position, as shown in FIG. 10. Then, when a tomographic image is generated from the calculated regression surface, as described later, the tomographic image includes an artifact at the pixel position corresponding to the outliers.

For this reason, the pixel value calculating unit 36 determines a pixel value which is largely different from the adjacent pixel values among the pixel values projected on the slice plane Tj as an outlier, and calculates the pixel value at each coordinate position of interest with removing the outlier pixel value. For example, the pixel value calculating unit 36 calculates a difference between each of the pixel values projected on the coordinate position of interest and an average value of pixel values at pixel positions adjacent to the coordinate position of interest on the slice plane Tj, and determines a pixel value whose difference from the average value exceeds a predetermined threshold value as an outlier to remove the outlier pixel value when the regression analysis is performed. In place of removing the outlier, the outlier pixel value may be assigned with a small weight.

Figure 11:
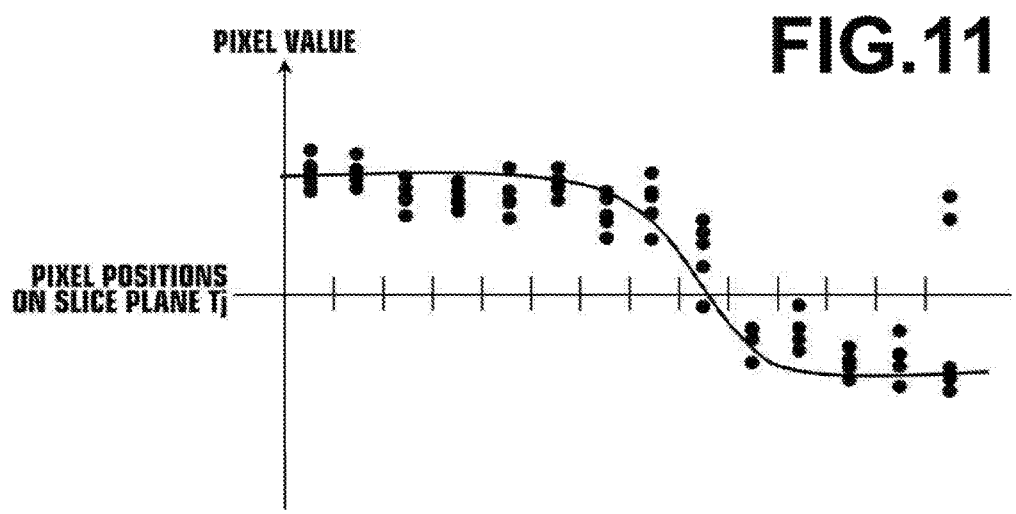
FIG. 11 is a diagram for explaining how a regression curve (regression surface) from which outliers are removed is generated.

When the regression curve (regression surface) is calculated with removing the outliers or assigning the outliers with a small weight, the value at the pixel position including the outliers does not differ largely from the value at the adjacent pixel position, as shown in FIG. 11. This allows preventing the tomographic image from including an artifact.

The operation to remove an outlier can be integrated into the regression analysis. In the case where the least squares method is used, the weighted least squares method shown by the equation (3) above may be used with assigning the outlier pixel values with a weight of 0 or a small weight. In the case where the moving average is used, a weighted average may be calculated with assigning the outlier pixel values with a weight of 0 or a small weight.

After the regression surface is generated, the pixel value calculating unit 36 samples the regression surface at a desired sampling interval to generate a band tomographic image TLj-k. The sampling interval may be stored in the storage 23 as a fixed value. The sampling interval may be changeable to an arbitrary value according to an instruction made via the input unit 4. For example, if the same sampling interval as that of the band projection images Li-k is set, the band tomographic image TLj-k has the same resolution as that of the band projection images Li-k. If the sampling interval is set smaller than that of the band projection images Li-k, the band tomographic image TLj-k has a higher resolution than that of the band projection images Li-k. In contrast, if the sampling interval is set greater than that of the band projection images Li-k, the band tomographic image TLj-k has a lower resolution than that of the band projection images Li-k. In this case, the value of the sampling interval stored in the storage 23 is rewritten according to input by the operator via the input unit 4 and the sampling interval is changed. Alternatively, the sampling interval may be adjusted depending on the resolution of the display unit 3.

The frequency synthesis unit 34 performs frequency synthesis on the band tomographic images TLj-k to generate a tomographic image TGj of the slice plane Tj of the subject. In this embodiment, each of the band tomographic images TLj-k for desired frequency bands is multiplied with a weight W to change the emphasis level, and then frequency synthesis of the band tomographic images TLj-k is performed to generate the tomographic image TGj of the slice plane Tj of the subject. It should be noted that, in this embodiment, the band tomographic images TLj-k for all the frequency bands are multiplied with the weights W to change the emphasis levels. For example, calcification in the breast M includes relatively small structures. In order to facilitate seeing such calcification in a tomographic image, the band tomographic images TLj-k for relatively high frequency bands are multiplied with weights W greater than one to emphasize and increase the pixel values of the band tomographic images TLj-k. On the other hand, relatively large structures, such as lumps of fat, in the breast M, as well as density irregularity in an image and discrepancy in density between images are contained in the band tomographic images TLj-k for relatively low frequency bands. In order to diminish the relatively large structures, as well as the density irregularity in an image and the discrepancy in density between images, the band tomographic images TLj-k for the relatively low frequency bands are multiplied with weights W smaller than one to diminish and reduce pixel values of the band tomographic images TLj-k. It should be noted that a weight W of one will result in substantially no change in the emphasis level. The low frequencies herein refers to frequencies that are set, as appropriate, within the range of 50% or less of the Nyquist frequency, which is determined by the spacing between the pixel positions of the band projection images Li-k.

Further, in this embodiment, while the pixel value projection unit 35 performs the smoothing to reduce noise in the band tomographic images TLj-k, the pixel value projection unit 35 may further reduce noise by multiplying the band tomographic images TLj-k for frequency bands that contain much noise with weights W smaller than one.

This allows further emphasizing a desired structure and reducing noise in a tomographic image that is generated as described later.

Figure 12:
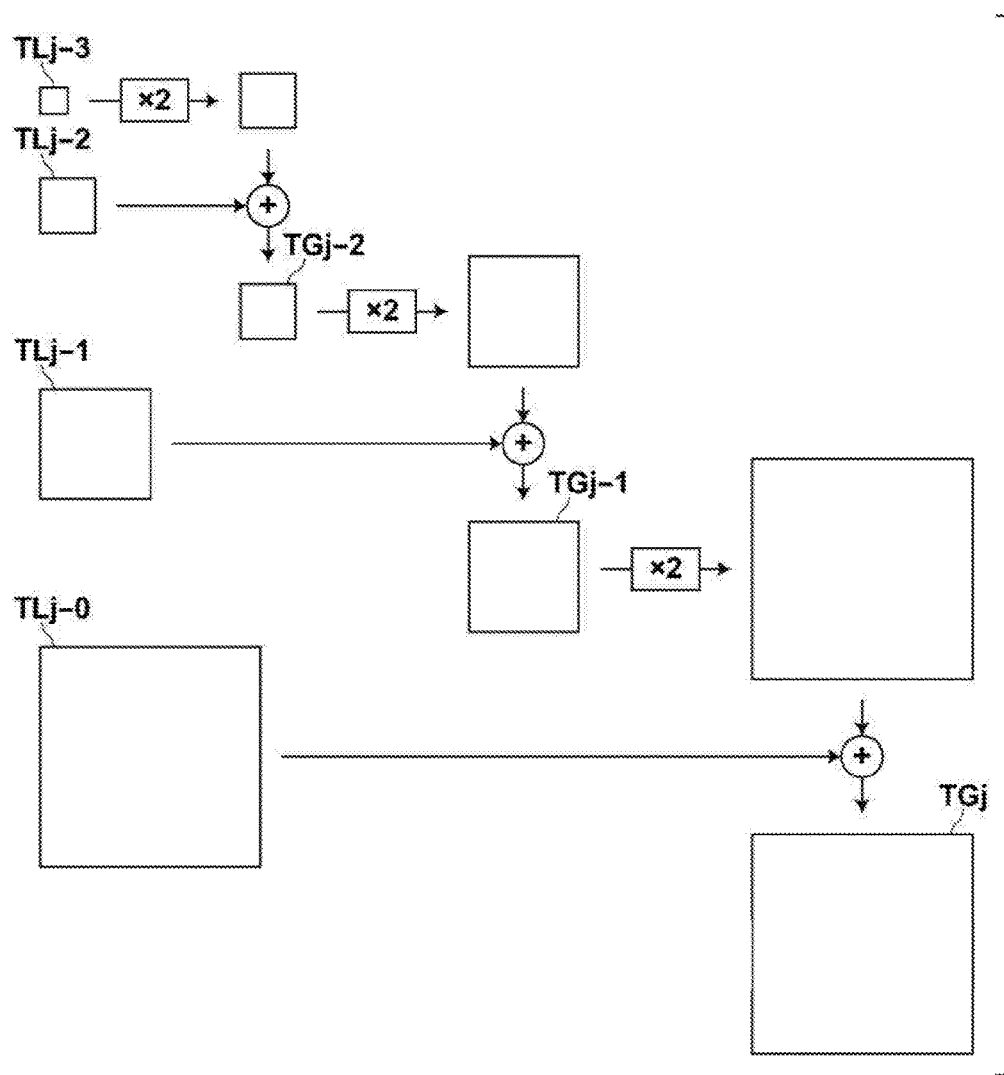
FIG. 12 is a diagram for explaining frequency synthesis in the first embodiment.

FIG. 12 is a diagram for explaining the frequency synthesis. It should be noted that, while the band tomographic images up to the band tomographic image TLj-10 for the 10th frequency band are generated in this embodiment, frequency synthesis starting from a band tomographic image TLj-3 for the 3rd frequency band is explained here for simplifying the explanation. In the example shown in FIG. 12, it is assumed that the band tomographic images TLj-k are multiplied with weights W.

The frequency synthesis unit 34 enlarges the band tomographic image TLj-3 for the 3rd frequency band twice by interpolation, and adds the thus enlarged band tomographic image TLj-3 to a band tomographic image TLj-2 for the 2nd frequency band to generate a tomographic image TGj-2. Then, the frequency synthesis unit 34 enlarges the tomographic image TGj-2 twice, and adds the thus enlarged tomographic image TGj-2 to a band tomographic image TLj-1 for the 1st frequency band to generate a tomographic image TGj-1. Further, the frequency synthesis unit 34 enlarges the tomographic image TGj-1 twice, and adds the thus enlarged tomographic image TGj-1 to a band tomographic image TLj-0 for the 0th frequency band to generate a tomographic image TGj-0, i.e., a tomographic image TGj.

Next, a process performed in the first embodiment is described. FIG. 13 is a flow chart showing the process performed in the first embodiment. In response to an instruction to start the process made by the operator and received by the input unit 4, the tomosynthesis imaging is performed, and the image obtaining unit 31 obtains a plurality of projection images Gi (step ST1). Then, the frequency decomposition unit 32 performs frequency decomposition on each of the projection images Gi to obtain band projection images Li-k representing frequency components for individual frequency bands for the projection image Gi (step ST2).

Subsequently, the pixel value projecting unit 35 of the reconstruction unit 33 projects pixel values of the band projection images Li-k on coordinate positions on a desired slice plane Tj of the breast M, while preserving the pixel values of the band projection images Li-k (step ST3).

Then, the pixel value calculating unit 36 performs the regression analysis on the pixel values of the band projection images Li-k projected on the slice plane Tj (step ST4) to generate a regression surface that represents each band tomographic image of the slice plane Tj (step ST5). Further, the pixel value calculating unit 36 samples the regression surface at a given sampling interval to generate each band tomographic image TLj-k (step ST6). Then, the frequency synthesis unit 34 performs frequency synthesis on the band tomographic images TLj-k to generate a tomographic image TGj of the slice plane Tj (step ST7), and the process ends. It should be noted that, when another tomographic image of a different slice plane is generated, the operations in steps ST1 to ST7 are performed with changing the position of the slice plane.

It should be noted that small structures in the subject are contained in band projection images for relatively high frequency bands, and large structures in the subject as well as the density irregularity in an image and the discrepancy in density between images are contained in band projection images for relatively low frequency bands. Reconstructing the band projection images Li-k for individual frequency bands as in this embodiment allows, with respect to the relatively high frequency bands, small structures in the subject to be projected to generate the band tomographic images without being influenced by large structures as well as the density irregularity and the discrepancy in density. Further, artifacts can be removed for each frequency band, and this allows reducing artifacts due to differences of the sizes of structures in the subject as well as the density irregularity and the discrepancy in density. Thus, according to this embodiment, tomographic images with higher image quality can be generated.

Further, in this embodiment, pixel values of the band projection images Li-k are projected on coordinate positions on a desired slice plane Tj of the breast M, which is the subject, based on the positional relationship between the position of the x-ray source 16 corresponding to each of the band projection images Li-k and the radiation detector 15, while preserving the pixel values of the band projection image Li-k. Then, the pixel value at each coordinate position of interest is calculated by generating a regression surface by regression analysis, for example, based on the pixel values of the band projection images Li-k projected in a predetermined range relative to the coordinate position of interest on the slice plane Tj, to generate a band tomographic image TLj-k. When compared with the conventional techniques where only the pixel values of the band projection images Li-k projected on each coordinate position of interest are used to calculate the pixel value at the coordinate position of interest, this embodiment allows taking the influence of pixel values around the coordinate position of interest into account, thereby reducing artifacts to allow generation of a band tomographic image TLj-k with even higher image quality, and in turn a tomographic image TGj with even higher image quality. Further, since it is not necessary to repeat projecting the pixel values again and again, which is necessary in the successive approximation reconstruction method, significant reduction of the calculation time can be achieved.

Further, band tomographic images TLj-k with a desired resolution, and in turn a tomographic image TGj with a desired resolution, can be generated by sampling the regression surface at a desired sampling interval and calculating the pixel value at each coordinate position of interest.

Next, a second embodiment of the disclosure is described. It should be noted that the configuration of the tomographic image generation device according to the second embodiment is the same as the above-described configuration of the tomographic image generation device according to the first embodiment, and only the process performed is different. Therefore detailed description of the device is omitted in the following description. In the above-described first embodiment, pixel values of each of the band projection images Li-k at positions intersecting with the straight lines that connect the radiation source position and the individual pixel positions on the slice plane Tj, as shown in FIG. 7, are projected as pixel values at the pixel positions on the slice plane Tj on the straight lines. Whereas, in the second embodiment, for each of the different radiation source positions Si, pixel values at pixel positions on each of the corresponding band projection images Li-k on straight lines that connect the radiation source position Si and the individual pixel positions on the band projection images Li-k are projected on coordinate positions on the slice plane Tj intersecting with the straight lines.

FIG. 14 is a diagram for explaining how the pixel values are projected in the second embodiment. It should be noted that FIG. 14 explains a case where a band projection image Li-k obtained at a radiation source position Si is projected on a desired slice plane Tj (j=1 to m, where m is the number of slice planes) among slice planes of the breast M. As shown in FIG. 14, in the second embodiment, pixel values at pixel positions of the band projection image Li-k on the straight lines that connect the radiation source position Si and the individual pixel positions on the band projection image Li-k are projected as pixel values at coordinate positions on the slice plane Tj intersecting with the straight lines. The relationship among the coordinates (sxi, syi, szi) of the radiation source position at the radiation source position Si, the coordinates Tj(tx, ty, tz) of a coordinate position on the slice plane Tj, and the coordinates Pi(pxi, pyi) of a pixel position Pi on the band projection image Li-k are as shown by the equations (1) above. Therefore the coordinate position on the slice plane Tj on which the pixel value at each pixel position on the band projection image Li-k is projected can be calculated by solving the equations (1) above for tx and ty, where pxi and pyi in the equations (1) are the pixel position on the band projection image Li-k. In this manner, each pixel value of each band projection image Li-k is projected on the calculated coordinate position on the slice plane Tj.

In this case, as shown in FIG. 14, intersection points Tjx between the slice plane Tj and the straight lines that connect the radiation source position Si and the individual pixel positions on the band projection image Li-k may not be pixel positions on the slice plane Tj. In this case, in the second embodiment, the pixel values of the band projection image Li-k are projected on coordinate positions between the pixel positions on the slice plane Tj. This means that, in the second embodiment, the pixel values of the band projection image Li-k are projected also on coordinate positions other than the pixel positions on the slice plane Tj.

Figure 15:
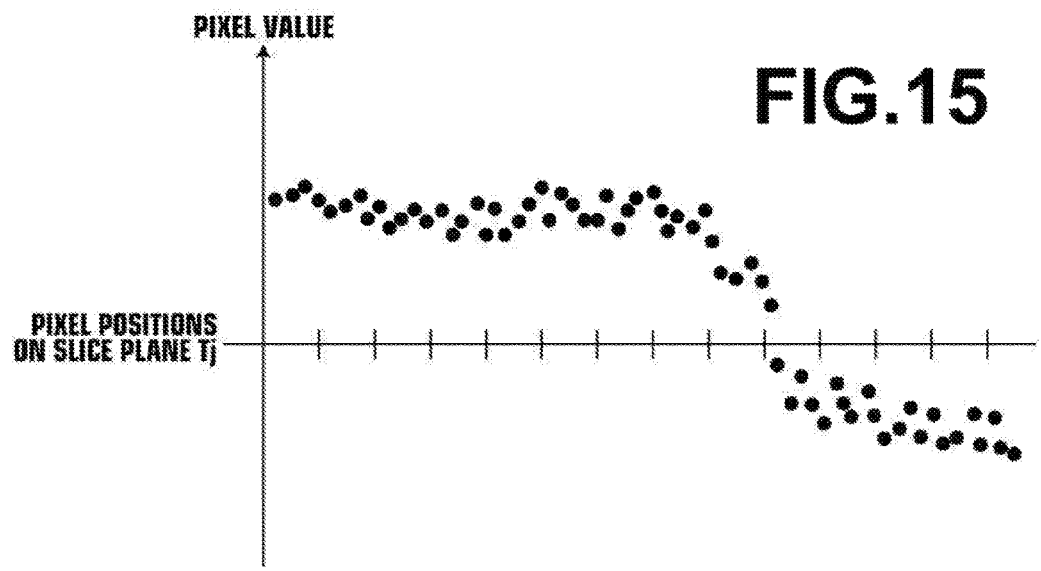
FIG. 15 is a diagram showing pixel values projected on a slice plane in the second embodiment.

In the second embodiment, the pixel value projecting unit 35 projects, for all the radiation source positions Si for each frequency band, the pixel values of all the band projection images Li-k on the slice plane Tj. Thus, pixel values of the band projection images Li-k corresponding to the number of pixels of all the projection images Gi are projected on coordinate positions including the pixel positions on the slice plane Tj, as shown in FIG. 15.

Similarly to the first embodiment, the pixel value calculating unit 36 in the second embodiment performs the filtering on the pixel values of the band projection images Li-k projected on the slice plane Tj, and performs the regression analysis to generate a regression surface. The filtering is performed with setting each coordinate position on the slice plane on which the pixel values are projected as the center.

In the second embodiment, since the pixel values of the band projection images Li-k are projected on coordinate positions on the slice plane Tj, as described above, it is not necessary to perform interpolation of the pixel values of the band projection images Li-k, which is necessary in the first embodiment. Compared with the first embodiment, image quality of the band projection images Li-k is not degraded when they are projected. This allows achieving even higher image quality of the generated band tomographic images TLj-k, and in turn the generated tomographic image TGj.

Further, in the second embodiment, a spacing between the coordinate positions on the slice plane Tj on which the pixel values are projected is smaller than a spacing between the pixel positions on the slice plane Tj, and coordinate positions other than the pixel positions on the slice plane Tj also have pixel values. This allows generating a highly accurate regression surface based on the actually obtained pixel values of the band projection images Li-k, even for a frequency band higher than the Nyquist frequency, which is determined by the spacing between the pixel positions on the slice plane Tj. Therefore, in the second embodiment, degradation of image quality of the band tomographic images TLj-k can be suppressed even when a small sampling interval of the regression surface is set, thereby allowing generation of a tomographic image TGj with even higher image quality.

Next, a third embodiment of the disclosure is described. It should be noted that the configuration of the tomographic image generation device according to the third embodiment is the same as the above-described configuration of the tomographic image generation device according to the first embodiment, and only the process performed is different. Therefore detailed description of the device is omitted in the following description. The difference between the third embodiment and the first embodiment lies in that, in the third embodiment, the image obtaining unit 31 further obtains a radiographic image by ordinary x-ray imaging, and the pixel value projecting unit 35 corrects projection positions on a slice plane Tj on which pixel values of the band projection images Li-k are projected. It should be noted that the "ordinary x-ray imaging" as used herein refers to x-ray imaging where the x-ray source 16 is not moved and is fixed at a given radiation source position, and the x-rays are applied to the subject under imaging conditions for obtaining a transmission image of the subject.

Figure 16:
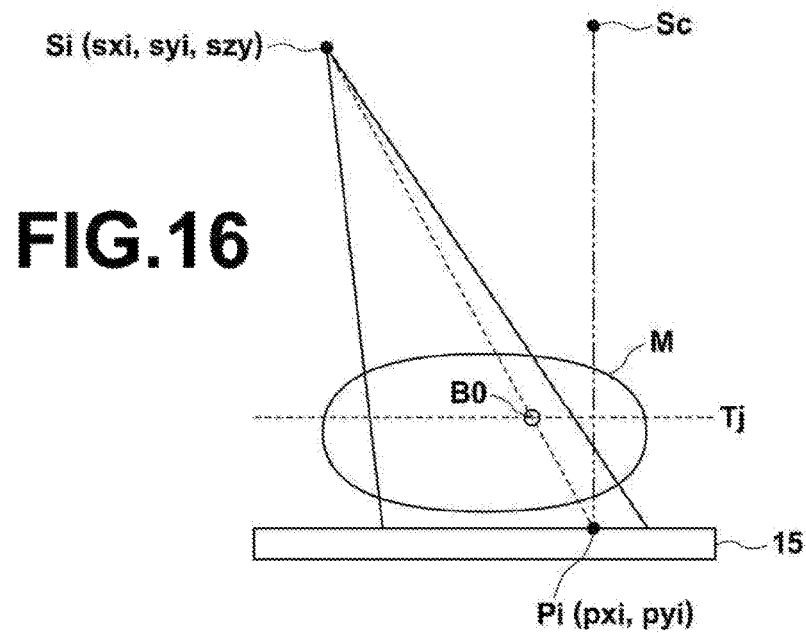
FIG. 16 is a diagram showing a positional relationship between the position of a structure on a slice plane and the position of the structure projected on a radiation detector.
Figure 17:
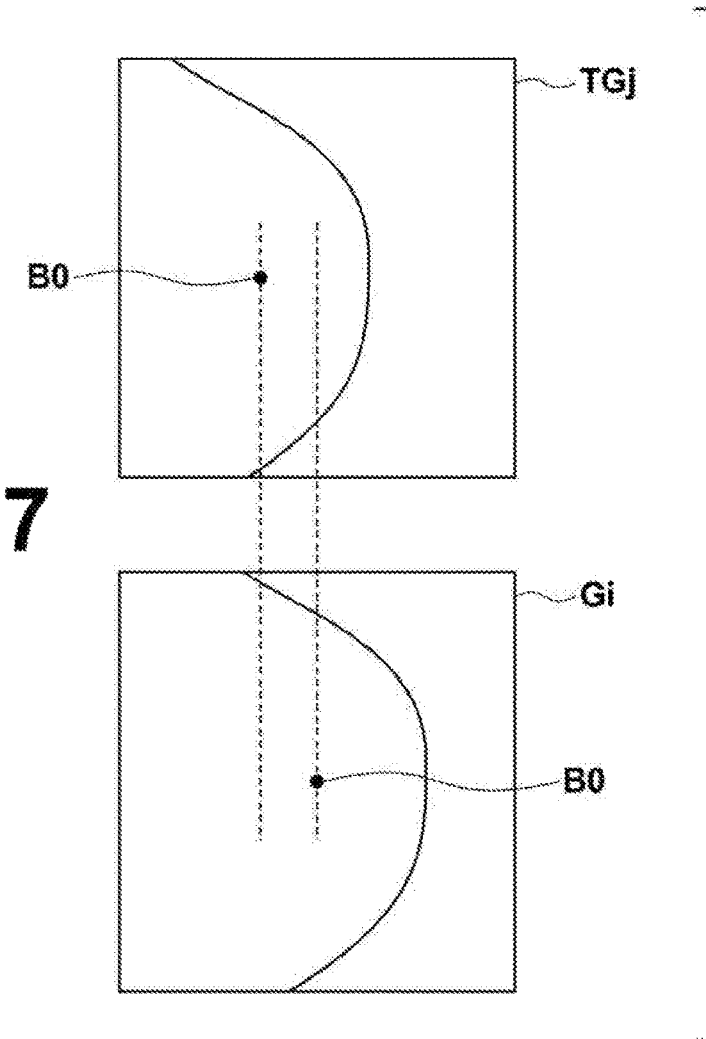
FIG. 17 is a diagram showing a difference between the position of a structure on a tomographic image and the position of the structure on a radiographic image.

As shown in FIG. 16, the x-rays emitted from the x-ray source 16 form a cone beam, which spreads as it travels away from the x-ray source 16. The position of the surface of the radiation detector 15, at which the projection images Gi are obtained, is farther from the x-ray source 16 than the slice plane Tj. Therefore when the breast M is imaged with a given radiation source position among different radiation source positions Si, the position of a structure B0, such as a mammary gland and calcification, included in the breast M on the projection image Gi detected by the radiation detector 15 is different from the position of the structure B0 in a tomographic image TGj of the slice plane Tj, as shown in FIG. 17.

When a radiographic image is obtained by the ordinary x-ray imaging, the position of the x-ray source 16 is fixed at a given radiation source position, and the breast M is imaged under imaging conditions for obtaining a transmission image of the breast M. Therefore the geometrical positional relationship of the projection image obtained with the given radiation source position is the same as that of the radiographic image. In this case, when the obtained radiographic image and the tomographic image are displayed side by side for diagnosis, the position of the structure B0 in the radiographic image differs from the position of the structure B0 in the tomographic image. In the third embodiment, the pixel value projecting unit 35 corrects the coordinate position on the slice plane Tj on which the pixel value at each coordinate position of interest of each band projection image Li-k is projected based on the positional relationship between the radiation source position Si with which the projection image Gi is taken and the coordinate position of interest on the projection image Gi, such that the coordinate position of interest on the band projection image Li-k agrees with the coordinate position on the slice plane Tj on which the pixel value at the coordinate position of interest is projected.

Now, how the projection positions are corrected is described. In the following description, correction of the projection positions for the band projection image Li-0 for the highest frequency band is described. As shown in FIG. 16, assuming that coordinates of the radiation source position at the radiation source position Si are (sxi, syi, szi), and coordinates of the structure B0 on the slice plane Tj are Tj(tx, ty, tz), then coordinates Pi(pxi, pyi) of the projection position on the radiation detector 15 on which the structure B0 is projected are expressed by the equations (1) above.

Assuming that Pi is the coordinate position of interest, if the coordinate positions are not corrected, the coordinate position of interest Pi of the band projection image Li-0 is projected on the coordinate position Tj(tx, ty, tz) on the slice plane Tj, and the coordinate position on the slice plane Tj on which the pixel value at the coordinate position of interest Pi is projected can be calculated by solving the equations (1) for tx and ty.

On the other hand, as shown in FIG. 16, when the x-ray source 16 is present on a line which is orthogonal to the detection surface of the radiation detector 15 and crosses the coordinate position Pi(pxi, pyi), the coordinate position of interest Pi is projected at the intersection point on the band tomographic image of the slice plane Tj between the slice plane Tj and the straight line that connects the radiation source position Sc and the coordinate position Pi. In this case, the position of the structure B0 on the tomographic image of the slice plane Tj is at the same two-dimensional coordinates as those on the band projection image Li-0, and the position of the structure B0 on the band projection image corresponding to the radiation source position Sc agrees with the position of the structure B0 on the tomographic image of the slice plane Tj. Therefore the coordinate position on the slice plane Tj on which the pixel value at the coordinate position of interest is projected is corrected by changing the radiation source position which serves as the reference when the pixel values of the band projection image are projected on the slice plane Tj to the radiation source position Sc, which is present on the straight line that is orthogonal to the coordinate position on the band projection image of the pixel value to be projected. Assuming that the coordinate position of the radiation source position Sc serving as the reference for the correction is (sxc, syc, szc), the relationship between the coordinate position of interest Pi and the coordinate position (tx,ty) on the slice plane Tj after the correction is expressed by the equation (6) below.

$$P_i(px_i, py_i) = \left( \frac{sz_i}{sz_i - tz} \frac{sz_c - tz}{sz_c} tx - \frac{tz}{sz_i - tz} sx_i + \frac{sz_i}{sz_i - tz} \frac{tz}{sz_c} sx_c, \right. \tag{6}$$
$$\left. \frac{sz_i}{sz_i - tz} \frac{sz_c - tz}{sz_c} ty - \frac{tz}{sz_i - tz} sy_i + \frac{sz_i}{sz_i - tz} \frac{tz}{sz_c} sy_c \right)$$

In the equation (6), $(sz_c - tz)/sz_c$ in the first term of the equation expressing each of pxi and pyi represents the enlargement factor at the coordinate position, and the third term represents the amount of shift of the coordinate position in the x direction or the y direction. Therefore the corrected coordinate position on the slice plane Tj on which the pixel value at the coordinate position of interest Pi is projected can be calculated by solving the equation (6) for tx and ty.

It should be noted that, by calculating the amount of shift of each coordinate position for the other frequency bands based on the amount of shift of the corresponding coordinate position calculated for the highest frequency band, corrected coordinate positions can be calculated similarly for the other frequency bands.

By correcting the coordinate positions on the slice plane Tj on which the pixel values of the band projection images Li-k are projected in this manner, the position of a structure, such as a tumor, included in the finally generated tomographic image TGj can be aligned with the position of the corresponding structure included in the projection image, i.e., the radiographic image. This allows more accurate diagnosis using the radiographic image and the tomographic image.

Next, a fourth embodiment of the disclosure is described. It should be noted that the configuration of the tomographic image generation device according to the fourth embodiment is the same as the above-described configuration of the tomographic image generation device according to the first embodiment, and only the process performed is different. Therefore detailed description of the device is omitted in the following description. The difference between the fourth embodiment and the first embodiment lies in that the frequency decomposition unit 32 according to the fourth embodiment performs frequency decomposition on the projection images Gi only with respect to the direction in which the x-ray source 16 is moved.

Figure 18:
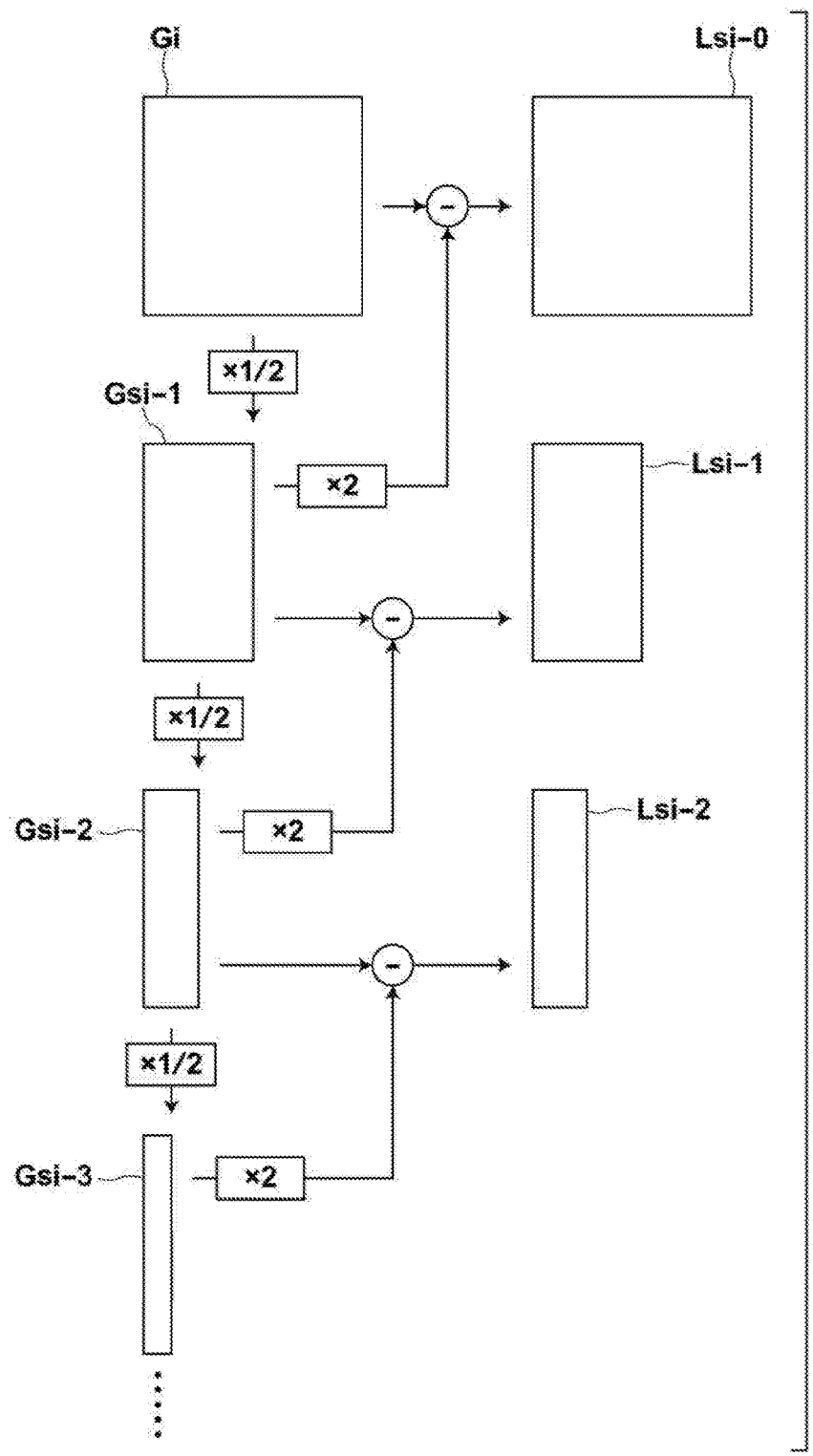
FIG. 18 is a diagram for explaining frequency decomposition in the fourth embodiment.

FIG. 18 is a diagram for explaining the frequency decomposition in the fourth embodiment. In the fourth embodiment, first, the frequency decomposition unit 32 filters a projection image Gi for a given frequency band with a Gaussian filter with σ=1, for example, to reduce the projection image Gi by half with respect to the direction in which the x-ray source 16 is moved to generate a reduced image Gsi-1 of Gaussian components. It should be noted that the direction in which the x-ray source 16 is moved corresponds to the horizontal direction in FIG. 18. The reduced image Gsi-1 corresponds to the projection image Gi reduced by half with respect to the direction in which the x-ray source 16 is moved. Then, the frequency decomposition unit 42 performs interpolation, such as third-order B-spline interpolation, to enlarge the reduced image Gsi-1 with respect to the direction in which the x-ray source 16 is moved such that the size of the reduced image Gsi-1 becomes the same as the size of the projection image Gi, and subtracts the thus enlarged reduced image Gsi-1 from the projection image Gi to generate a band projection image Lsi-0 of Laplacian components for the highest frequency band.

Subsequently, the frequency decomposition unit 42 filters the reduced image Gsi-1 with a Gaussian filter with σ=1 to reduce the reduced image Gsi-1 by half with respect to the direction in which the x-ray source 16 is moved to generate a reduced image Gsi-2, and enlarges the reduced image Gsi-2 twice with respect to the direction in which the x-ray source 16 is moved such that the size of the reduced image Gsi-2 becomes the same as the size of the reduced image Gsi-1. Then, the frequency decomposition unit 42 subtracts the thus enlarged reduced image Gsi-2 from the reduced image Gsi-1 to generate a band projection image Lsi-1 for the 1st frequency band. The above-described operations are repeated until band projection images for desired frequency bands are generated, to thereby generate band projection images Lsi-k (where k=0 to a, where a is the number of bands) for a plurality of frequency bands. It should be noted that the band projection images Lsi-k for different frequency bands may be generated by using a different multi-resolution conversion technique, such as wavelet transform.

The operations performed by the reconstruction unit 33 and the frequency synthesis unit 34 in the fourth embodiment are the same as those in the above-described first embodiment, except that the band projection images are the band projection images Lsi-k that are generated by frequency decomposition with respect to the direction in which the x-ray source 16 is moved, and therefore are not described in detail here.

In this manner, in the fourth embodiment, each of the projection images Gi is subjected to frequency decomposition only with respect to the direction in which the x-ray source 16 is moved, and this allows reducing the amount of calculation for the frequency decomposition and the frequency synthesis.

Further, when the band projection images Li-k are reconstructed, in particular, using a filtered back projection method, filtering is performed with respect to a direction that is moved relative to the direction in which the x-ray source 16 is moved to reduce blur with respect to the direction in which the x-ray source 16 is moved. In this case, by preforming the frequency decomposition with respect to the direction in which the x-ray source 16 is moved, in particular, to emphasize band tomographic images TLj-k for desired frequency bands, filtering during the reconstruction can be omitted. This allows reduction of processing time for the reconstruction.

Next, a fifth embodiment of the disclosure is described. FIG. 19 is a diagram illustrating the schematic configuration of a tomographic image generation device according to the fifth embodiment. It should be noted that the elements shown in FIG. 19 that are the same as those shown in FIG. 3 are denoted by the same reference numerals and are not described in detail here. The difference between the fifth embodiment and the first embodiment lies in that the tomographic image generation device according to the fifth embodiment includes a pseudo image generating unit 37 for generating a pseudo image from a plurality of tomographic images of a plurality of slice planes of the breast M.

The pseudo image generating unit 37 generates as the pseudo image an addition tomographic image by adding up values at corresponding pixel positions of a plurality of tomographic images TGj generated for a plurality of slice planes Tj. The thus generated addition tomographic image shows a pseudo transmission image of the subject, which appears as the same as a radiographic image obtained by the ordinary x-ray imaging. In this embodiment, noise in the band projection images is reduced when the regression surface is generated, and small emphasis levels are set for band tomographic images for frequency bands that contain much noise during the frequency synthesis, and thus the tomographic images have high image quality with reduced noise. By adding up such tomographic images, a high quality transmission image, i.e., a high quality pseudo radiographic image, can be generated.

In the fifth embodiment, when the pixel values of the band projection images are projected on coordinate positions on each slice plane, the coordinate positions on the slice plane Tj are corrected similarly to the third embodiment to align the position of a corresponding structure among the tomographic images. This facilitates determining corresponding pixel values to perform the addition, thereby allowing generation of a radiographic image with even higher image quality.

It should be noted that, in place of an addition tomographic image, the pseudo image generating unit 37 may generate as the pseudo image a maximum projection image, which is obtained by an MIP method that extracts maximum values from the corresponding pixel positions of the plurality of tomographic images. Alternatively, the pseudo image generating unit 34 may generate as the pseudo image a minimum projection image, which is obtained by a minIP method that extracts minimum values from the plurality of tomographic images.

When the generated tomographic image is displayed on the display unit 3 in the above-described embodiments, an instruction to change the size of an area of interest on the tomographic image may be received to display an enlarged image of the area of interest for which the instruction to change the size is received. In this case, an area of the regression surface corresponding to the area of interest for which the instruction to change the size has been received is extracted, and a sampling interval which is smaller than the sampling interval of the tomographic image is set to sample the extracted area to generate the band tomographic images of the area of interest. Then, the reconstruction and the frequency synthesis are performed on the band tomographic images of the area of interest. This allows displaying an enlarged image A2 of an area of interest A1 specified on the tomographic image TGj, as shown in FIG. 20. The sampling interval here is preferably a sampling interval that is determined according to the resolution of the display unit 3. While the enlarged image A2 shown in FIG. 20 is superimposed on the tomographic image TGj, the enlarged image A2 may be displayed in place of the tomographic image TGj, or the enlarged image A2 may be displayed side by side with the tomographic image TGj. In a case where an instruction to reduce an area of interest is made, a sampling interval that is greater than the sampling interval of the tomographic image is set to sample the extracted area of the regression surface corresponding to the area of interest.

Figure 21:
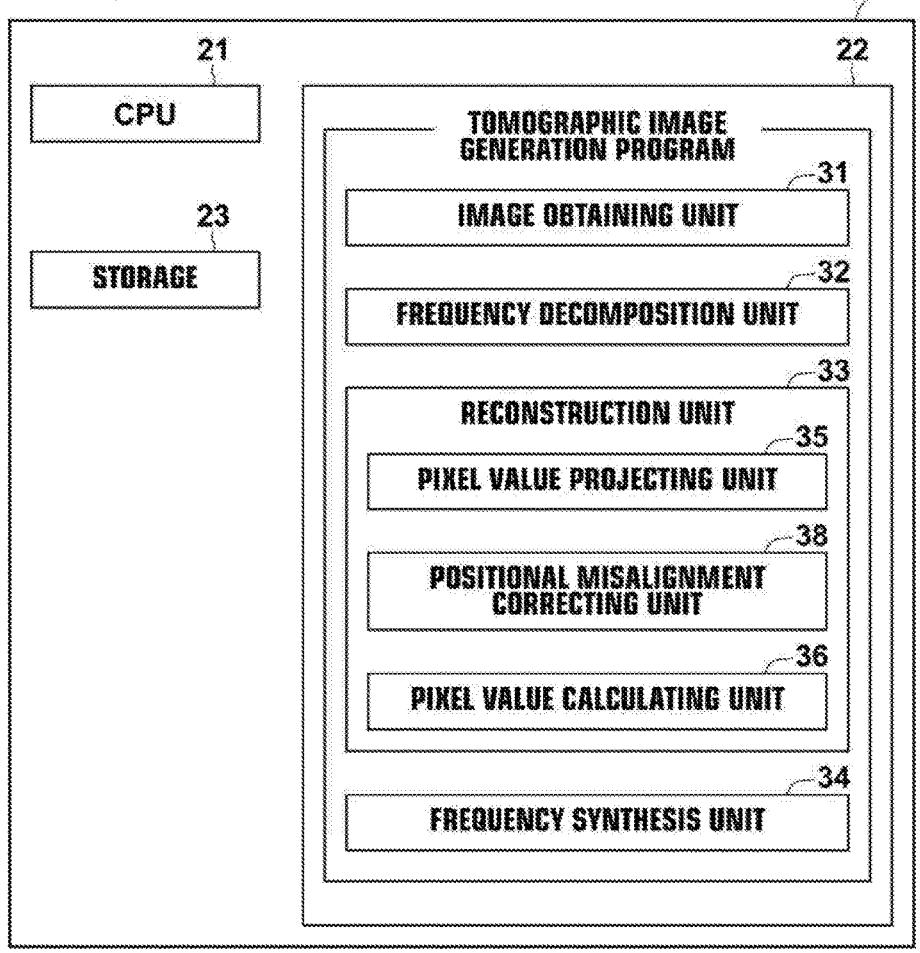
FIG. 21 is a diagram illustrating the schematic configuration of a tomographic image generation device of a sixth embodiment implemented by installing a tomographic image generation program on a computer.

Next, a sixth embodiment of the disclosure is described. FIG. 21 is a diagram illustrating the schematic configuration of a tomographic image generation device according to the sixth embodiment. It should be noted that the elements shown in FIG. 21 that are the same as those shown in FIG. 3 are denoted by the same reference numerals and are not described in detail here. The difference between the sixth embodiment and the first embodiment lies in that the tomographic image generation device according to the sixth embodiment includes a positional misalignment correcting unit 38 for correcting for positional misalignment between a plurality of band slice plane projection images Gti-k for the individual frequency bands, each band slice plane projection image Gti-k being defined as an image formed by pixel values of each of the band projection images Li-k projected on the slice plane Tj.

When the tomosynthesis imaging is performed, it is difficult to accurately move the radiation source to the calculated radiation source positions, due to influence of mechanical errors, such as vibration during imaging or mechanical misalignment, and the radiation source positions during imaging may be different from the calculated radiation source positions. This positional error, or positional misalignment, hinders accurate alignment of the projection position of an object, resulting in degradation of the image quality of the tomographic image.

Further, when the tomosynthesis imaging is performed, a plurality of images of the subject are taken based on an instruction to start an imaging operation, and this imaging operation takes several seconds from the start to the end of the imaging operation, during which the subject may move. When there is such a body motion of the subject, it is difficult to accurately align the projection position of the object during the reconstruction, resulting in degradation of the image quality of the tomographic image.

Furthermore, the influence of mechanical errors and body motions appears three-dimensionally and non-linearly in the subject, and it is difficult to remove the influence of mechanical errors and body motions from the tomographic image by simply translating, rotating, and enlarging or reducing the band projection images Li-k by affine transformation, etc.

Figure 22:
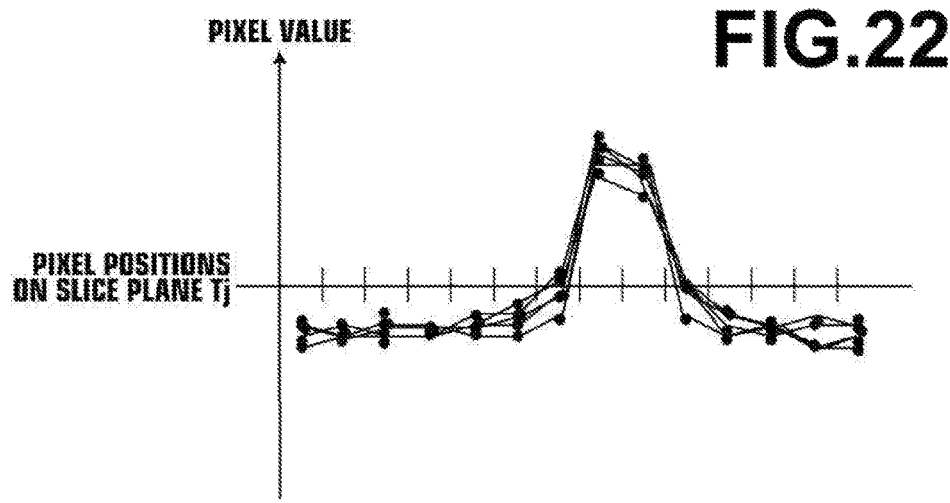
FIG. 22 shows a plurality of slice plane projection images without positional misalignment.
Figure 23:
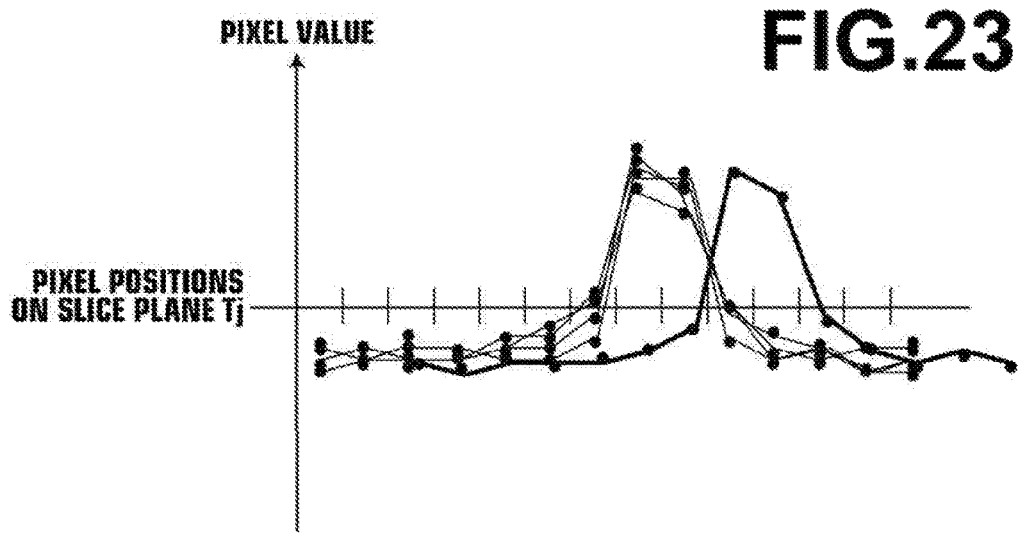
FIG. 23 shows a plurality of slice plane projection images with positional misalignment.
Figure 24:
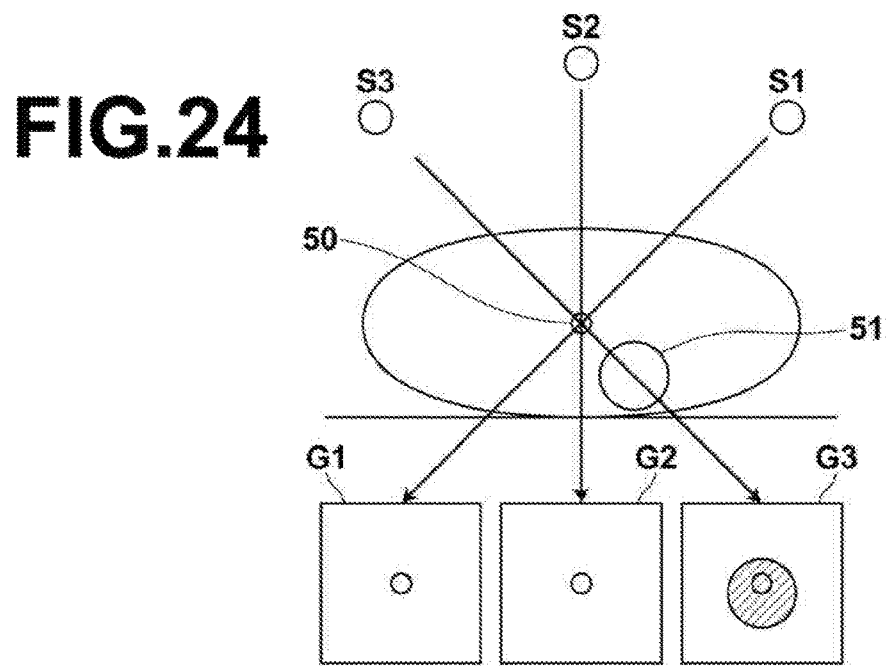
FIG. 24 is a diagram illustrating differences in projection images due to different radiation source positions.

In the sixth embodiment, the positional misalignment correcting unit 38 corrects for the positional misalignment between the band slice plane projection images Gti-k for the individual frequency bands. If there is no mechanical error and no body motion of the breast M during the imaging operation with moving the x-ray source 16 to different radiation source positions Si, pixel values of the band slice plane projection images Gti-k substantially agree with one another, as shown in FIG. 22. On the other hand, if there is a mechanical error or a body motion, a slice plane projection image corresponding to a projection image that is taken when the mechanical error or the body motion occurs has pixel positions that are shifted from the corresponding pixel positions of the other slice plane projection images, as shown in FIG. 23. The positional misalignment correcting unit 38 corrects for the positional misalignment between the band slice plane projection images Gti-k for the individual frequency bands such that the positions of the band slice plane projection images Gti-k agree with one another. Specifically, the positional misalignment correcting unit 38 detects feature points, such as an edge, an intersection point between edges, a corner of an edge, etc., included in each band slice plane projection image Gti-k by using an algorithm such as SIFT (Scale-Invariant Feature Transform) or SURF (Speeded Up Robust Features), and transforms the band slice plane projection images Gti-k such that the detected feature points agree among them, to thereby correct for the positional misalignment. Thus, the positional misalignment between the band slice plane projection image Gti-k is corrected, as shown in FIG. 22, and the distributions of pixel values on the band slice plane projection images Gti-k substantially agree with one another.

It should be noted that the SIFT is a technique that describes feature quantities which are invariant to rotation and scaling of an image at feature points, and aligns the positions of a plurality of images based on the described feature quantities. The SURF is a technique for more quickly achieving the alignment by substituting the operation performed in the SIFT with approximation. It should be noted that the operation to correct for positional misalignment performed in this embodiment is not limited to the SIFT or SURF, and any other suitable technique may be used.

In the sixth embodiment, after the correction of the positional misalignment between the band slice plane projection images Gti-k for the individual frequency bands, the pixel value calculating unit 36 generates band tomographic images DLj-k by calculating the pixel values on the slice plane Tj, similarly to the above-described embodiments. Then, the frequency synthesis is performed on the band tomographic images DLj-k to generate a tomographic image TGj.

As described above, in the sixth embodiment, positional misalignment between the band slice plane projection images Gti-k projected on the slice plane Tj is corrected. Thus, the influence of three-dimensional mechanical errors and three-dimensional body motions can be handled only as two-dimensional positional misalignment on the slice plane Tj. This allows effectively removing the positional misalignment on the slice plane Tj due to mechanical errors and body motions, thereby improving the image quality of the band tomographic images DLj-k, and in turn the image quality of the tomographic image TGj.

It should be noted that, in the tomographic images of adjacent slice planes, the corresponding pixel positions tend to have the same pixel value. For this reason, in the above-described embodiments, a plurality of regression surfaces of a plurality of slice planes of the breast M may be generated for the individual frequency bands, and the regression surface of a slice plane of interest may be smoothed using the regression surfaces of the adjacent slice planes. Specifically, for a regression surface of a slice plane Tj, a correlation among pixel values at corresponding pixel positions on regression surfaces of three adjacent slice planes Tj−1, Tj, and Tj+1 is calculated. Then, if the correlation exceeds a predetermined threshold value, smoothing is performed for the pixel position on the slice plane Tj by calculating an average of the pixel values at the pixel position of the three slice planes Tj−1, Tj, and Tj+1, for example. As the correlation, absolute difference values between the pixel values at the corresponding pixel positions can be used, for example. This allows taking the influence of pixel values of adjacent slice planes into account, thereby allowing generation of high image quality band tomographic images DLj-k with even reduced noise, and in turn a high image quality tomographic image with even reduced noise.

Further, after the regression surface is generated in the above-described embodiments, the regression surface may be modified by calculating an absolute difference value between each pixel value projected on each coordinate position on the slice plane Tj and the value of the regression surface at the corresponding coordinate position, determining a pixel value whose absolute difference value exceeds a predetermined threshold value as an outlier, and removing the outlier or assigning the outlier with a small weight. For example, in the case where the regression curve as shown in FIG. 10 is generated, an absolute difference value between each of the five pixel values projected on the rightmost pixel position on the slice plane Tj and the value of the regression curve at the corresponding pixel position is calculated. In this case, the absolute difference values of the two pixel values having the large values exceed the threshold value. Then, the two pixels having the large values are removed as outliers or assigned with a small weight to modify the regression curve. This allows generating a regression curve, as shown in FIG. 11, where the value at the pixel position including the outliers does not largely differ from the value at the adjacent pixel position.

Further, while the regression surface is generated after the pixel values of all the band projection images Li-k for each frequency band are projected on the slice plane Tj in the above-described embodiments, the regression surface may be generated for each band projection image Li-k. In this case, a correlation at corresponding coordinate positions among the regression surfaces calculated for the individual band projection images Li-k is calculated. As the correlation, absolute difference values can be used. Then, if there is a regression surface having a small correlation, i.e., having a pixel value whose absolute difference value exceeds a predetermined threshold value, the pixel value of the regression surface at the coordinate position with the small correlation is determined as an outlier and is removed or assigned with a small weight, and then a regression surface is generated based on pixel values of all the band projection image Li-k for each frequency band projected on coordinate positions on the slice plane Tj.

In the above-described embodiments, generation of the regression surface may be sequentially iterated. For example, after a regression surface is generated with the above-described technique for calculating a regression surface using the weighted least squares method, a weight wk for each observation point uk is calculated according to the equation (7) below. In the equation (7), f(uk) is a value at the observation point uk on the calculated regression curve.

$$\text{wk} = e^{-(qk - f(uk))^2} \quad (7)$$

According to the equation (7), the larger the difference between the observed value qk and value at the observation point uk on the regression curve, the smaller the value of the weight k. Then, the calculated weight wk is used to generate a regression curve according to the equation (3) above, and the newly generated regression curve is generated such that the influence of outliers is smaller than that in the previously generated regression curve. In particular, when there are outliers, smaller weights are assigned to the outliers, and this allows reducing artifacts at pixel positions with the outliers when the band tomographic images DLj-k, and in turn the tomographic image TGj, are generated. It should be noted that the number of iterations of the operation to generate the regression surface may be set in advance, or the operation may be iterated until a predetermined convergence condition is met. As the convergence condition, a condition such that a difference resulting from the iterative operation, i.e., the value of qk−f(uk), is not greater than a predetermined threshold value may be used.

It should be noted that the operation to generate the regression curve may also be sequentially iterated when the regression surface is generated using moving average or a kernel function. When moving average is used, the weight for each observation point uk is calculated similarly to the above-described equation (7), and calculation of the weighted moving average is iterated. With the technique using a kernel function, a term for calculating the weight wk, as in equation (7), is combined into the equation for determining the kernel, and the technique using the kernel function is iterated to generate a regression curve.

While each band tomographic image TLj-k is generated by generating a regression surface by the pixel value calculating unit 36 in the above-described embodiments, each band tomographic image TLj-k may be generated by calculating pixel values at pixel positions on the slice plane Tj by regression analysis, without generating a regression surface. In this case, the sampling interval for the band tomographic image TLj-k to be generated is set in advance, and each coordinate position corresponding to the sampling interval is set as the pixel position of interest on the slice plane Tj to calculate the pixel value at the pixel position of interest by the regression analysis.

While the reconstruction unit 33 in the above-described embodiments includes the pixel value projection unit 35 and the pixel value calculation unit 36 to generate a regression surface to generate each band tomographic image TLj-k, each band tomographic image TLj-k may be generated by reconstructing the band projection images Li-k for each frequency band using other reconstruction methods, such as a shift-and-add method, a back projection method such as a simple back projection method or a filtered back projection method, an algebraic reconstruction method, or a successive approximation reconstruction method.

In particular, in the case where the reconstruction is performed using the filtered back projection method, generating the band projection images Li-k as in the fourth embodiment allows omitting filtering with respect to a direction that is moved relative to the direction in which the x-ray source 16 is moved. This allows reduction of operation time for the reconstruction.

Further, while the subject of the tomosynthesis imaging in the above-described embodiments is the breast M, the disclosure is also applicable to tomosynthesis imaging with a subject other than a breast.

While only the x-ray source 16 is moved in the above-described embodiments, some imaging apparatuses allow moving the x-ray source 16 and the radiation detector 15 synchronously with each other. In this case, the x-ray source 16 and the radiation detector 15 may be moved synchronously with each other. Alternatively, the x-ray source 16 may be fixed and only the radiation detector 15 may be moved.

While the disclosure is applied to an imaging apparatus that performs tomosynthesis imaging in the above-described embodiments, the disclosure is applicable to any imaging apparatus that obtains a plurality of projection images by imaging a subject with different radiation source positions. For example, the disclosure is applicable to a CT imaging apparatus, where the radiation source and the radiation detector are disposed to face each other with the subject being the center, and the set of the radiation source and the radiation detector is rotated around the subject to obtain a plurality of projection images while applying radiation from different angles.

While the trajectory of the x-ray source 16 is a circular arc in the above-described embodiments, the trajectory of the x-ray source 16 may be a straight line.

Now, advantageous effects of the embodiments of the disclosure are described.

In the case where the frequency decomposition is performed on each of the projection images with respect to a specific direction on the projection image, the amount of calculation for the frequency decomposition and the frequency synthesis can be reduced.

When the band projection images are reconstructed, in particular, using the filtered back projection method, filtering is performed with respect to a direction in which the radiation source is moved relative to the detection unit to reduce blur with respect to the direction in which the radiation source is moved. In this case, in particular, in the case where the band tomographic images for desired frequency bands are emphasized using a filter, setting the specific direction as the direction in which the radiation source is moved relative to the detection unit allows omitting filtering during the reconstruction, and this allows reducing processing time for the reconstruction.

In the case where the emphasis levels for the band tomographic images for desired frequency bands are changed, the band tomographic images for the desired frequency bands can be emphasized or diminished. When the band tomographic images for the desired frequency bands are emphasized, a tomographic image where, in particular, a structure desired to be observed is emphasized can be generated. When the band tomographic images for the desired frequency bands are diminished, the band tomographic images for, in particular, frequency bands that are regarded as noise can be diminished, and this allows generating a high image quality tomographic image with low noise.

In the case where pixel values of the band projection images are projected on coordinate positions on a desired slice plane of the subject based on a positional relationship between the radiation source position during imaging corresponding to each of the band projection images and the detecting unit, while preserving the pixel values of the band projection images, a pixel value at each coordinate position of interest is calculated based on the pixel values of the band projection images projected in a predetermined range relative to the coordinate position of interest on the slice plane to thereby generate the band tomographic images, and a tomographic image is generated by performing frequency synthesis on the band tomographic images, influence of pixel values around the coordinate position of interest can be taken into account, unlike the conventional techniques where the pixel value at each coordinate position of interest is calculated using only pixel values of the projection images projected at the coordinate position of interest. This allows reducing artifacts to generate a tomographic image with higher image quality. Further, since it is not necessary to repeat the projection again and again, which is necessary in the successive approximation reconstruction method, significant reduction of the calculation time can be achieved.

In the case where, for each of the different radiation source positions, pixel values at pixel positions on the corresponding band projection image on straight lines that connect the radiation source and the individual pixel positions on the band projection image are projected as pixel values at coordinate positions on the slice plane at which the slice plane intersects with the straight lines, it is not necessary to perform interpolation of the pixel values when the pixel values are projected. This allows generating the band tomographic images with even higher image quality, and in turn the tomographic image with even higher image quality. In particular, since the pixel values are also projected on coordinate positions on the slice plane that are different from coordinate positions corresponding to pixel positions of the band tomographic image, high resolution band tomographic images with high image quality, and in turn a high resolution tomographic image with high image quality, can be generated.

In the case where the pixel values at the pixel positions on the slice plane are calculated by performing the regression analysis to generate a regression surface that represents each band tomographic image of the slice plane, and sampling the regression surface at a desired sampling interval, each band tomographic image with a desired resolution, and in turn a tomographic image with a desired resolution can be generated.

Further, when the regression analysis is performed, changing the sharpness of the pixel value at each coordinate position of interest allows emphasizing the sharpness of the pixel value at the coordinate position of interest or reducing the sharpness to achieve smoothing to suppress noise. This allows generating a tomographic image with desired image quality.

In the case where the level of change of the sharpness is changed depending on information about at least one of the imaging conditions during imaging and a structure of the subject included in the projection images, a tomographic image with desired image quality depending on at least one of the imaging conditions and the structure of the subject can be generated.

In the case where the pixel value at each coordinate position of interest is calculated with removing an outlier pixel value among pixel values of the band projection images projected in a predetermined range relative to the coordinate position of interest or assigning the outlier pixel value with a small weight, influence of the pixel value which is highly possible to be an artifact can be reduced, thereby allowing generation of a tomographic image with even higher image quality.

Farther, the radiation emitted from the radiation source is a cone beam, which spreads as it travels away from the radiation source. Since the position of the surface of the detecting unit, at which the projection images are obtained, is farther from the radiation source than the slice plane, the two-dimensional coordinate position of a structure included in the subject in each projection image differs from the position of the structure in the tomographic image of the slice plane.

In this case, the two-dimensional coordinate position of a structure included in the subject in the tomographic image can be made agree with the two-dimensional coordinate position of the structure in the projection image obtained with a given radiation source position by correcting a coordinate position on the slice plane on which the pixel value at each coordinate position of interest is projected based on the positional relationship between the given radiation source position and the coordinate position of interest, such that the two-dimensional coordinates of the coordinate position of interest on the band projection images for the individual frequency bands generated from the projection image obtained with the given radiation source position agrees with the two-dimensional coordinates of the coordinate position on the slice plane on which the pixel value at the coordinate position of interest is projected, and projecting the pixel values of the band projection images on the corrected coordinate positions on the slice plane.

Then, in the case where a radiographic image is obtained by imaging the subject with the given radiation source position, the band tomographic images, and in turn the tomographic image, are generated by calculating the pixel value at each coordinate position of interest on the slice plane with the pixel values of the band projection images being projected on the corrected coordinate positions, and the radiographic image and the tomographic image are displayed, the two-dimensional coordinate position of a structure included in the subject in the displayed radiographic image agrees with the two-dimensional coordinate position of the structure in the displayed tomographic image. This allows more appropriate diagnosis.

In the case where tomographic images for a plurality of slice planes of the subject are generated, and a pseudo image is generated from the tomographic images, a pseudo image with higher image quality can be generated.

What is claimed is:

1. A tomographic image generation device comprising:
at least one hardware processor configured to implement:
an image obtaining unit that obtains a plurality of projection images corresponding to different radiation source positions, the projection images being taken by moving a radiation source relative to a detector and applying radiation to a subject from the different radiation source positions to which the radiation source is moved;
a frequency decomposition unit that performs frequency decomposition on each of the projection images to obtain a plurality of band projection images representing frequency components for individual frequency bands for each of the projection images;
a reconstruction unit that reconstructs the band projection images for the individual frequency bands to generate band tomographic images of the subject; and
a frequency synthesis unit that performs frequency synthesis on the band tomographic images to generate a tomographic image of the subject,
wherein the reconstruction unit comprises:
a pixel value projecting unit for projecting pixel values of the band projection images onto coordinate positions of interest on a desired slice plane of the subject based on a positional relationship between each radiation source position during imaging corresponding to the band projection images and the detector, while preserving the pixel values of the band projection images; and
a pixel value calculating unit for calculating a pixel value at each of the coordinate positions of interest on the desired slice plane based on the pixel values of the band projection images projected in a predetermined range relative to each coordinate position of interest on a slice plane to generate the band tomographic images of each slice plane,
wherein the pixel value projecting unit projects, for each of the different radiation source positions, interpolated pixel values at coordinate positions on the band projection images intersecting with straight lines that connect each radiation source position and individual pixel positions on each desired slice plane as pixel values at the individual pixel positions on each desired slice plane on the straight lines.

2. The tomographic image generation device as claimed in claim 1, wherein the frequency decomposition unit performs frequency decomposition on each of the projection images with respect to a specific direction on the projection image.

3. The tomographic image generation device as claimed in claim 2, wherein the specific direction is a direction in which the radiation source is moved relative to the detector.

4. The tomographic image generation device as claimed in claim 1, wherein the at least one hardware processor is further configured to implement an emphasis level changing unit that changes emphasis levels for the band tomographic images for desired frequency bands,
wherein the frequency synthesis unit performs frequency synthesis on the band tomographic images for the individual frequency bands including the band tomographic images with the changed emphasis levels to generate the tomographic image.

5. The tomographic image generation device as claimed in claim 4, wherein the emphasis level changing unit makes the emphasis levels for the band tomographic images for the desired frequency bands higher than the emphasis levels for the band tomographic images in frequency bands different from the desired frequency bands.

6. The tomographic image generation device as claimed in claim 4, wherein the emphasis level changing unit makes the emphasis levels for the band tomographic images for the desired frequency bands lower than the emphasis levels for the band tomographic images other than those for the desired frequency bands.

7. The tomographic image generation device as claimed in claim 1, wherein the pixel value projecting unit projects, for each of the different radiation source positions, pixel values at pixel positions on the corresponding band projection image on straight lines that connect the radiation source position and the individual pixel positions on the band projection image as pixel values at coordinate positions on the slice plane intersecting with the straight lines.

8. The tomographic image generation device as claimed in claim 7, wherein a spacing between coordinate positions on the slice plane is smaller than a spacing between pixel positions on the slice plane.

9. The tomographic image generation device as claimed in claim 1, wherein the pixel value calculating unit calculates each pixel value at each coordinate position of interest by performing regression analysis on the pixel values of the band projection images projected on the slice plane.

10. The tomographic image generation device as claimed in claim 9, wherein the pixel value calculating unit calculates pixel values at pixel positions on the slice plane by performing the regression analysis to generate a regression surface that represents each band tomographic image of the slice plane, and sampling the regression surface at a desired sampling interval, to thereby generate each band tomographic image.

11. The tomographic image generation device as claimed in claim 10, wherein the sampling interval is different from a sampling interval of the band projection images.

12. The tomographic image generation device as claimed in claim 10, wherein, if an instruction to change the size of an area of interest in the tomographic image being displayed is received, the pixel value calculating unit generates a tomographic image of the area of interest with changing the sampling interval of an area of each regression surface corresponding to the area of interest according to the instruction to change.

13. The tomographic image generation device as claimed in claim 9, wherein the pixel value calculating unit changes sharpness of the pixel value at the coordinate position of interest when the regression analysis is performed.

14. The tomographic image generation device as claimed in claim 13, wherein the pixel value calculating unit changes a level of change of the sharpness depending on information of at least one of imaging conditions during the imaging and a structure of the subject included in the band projection images.

15. The tomographic image generation device as claimed in claim 1, wherein the pixel value calculating unit calculates the pixel value at the coordinate position of interest with removing an outlier pixel value among the pixel values of the band projection images projected in the predetermined range relative to the coordinate position of interest or assigning the outlier pixel value with a small weight.

16. The tomographic image generation device as claimed in claim 1, wherein the pixel value projecting unit corrects, based on a positional relationship between a given radiation source position and each coordinate position of interest on each of the band projection images for the individual frequency bands corresponding to the given radiation source position, coordinate positions on the desired slice plane on which a pixel value at the coordinate position of interest on the band projection image is projected such that two-dimensional coordinates of the coordinate position of interest on the band projection image agrees with two-dimensional coordinates of one of the coordinate positions on the slice plane on which the pixel value at the coordinate position of interest on the band projection image is projected, and projects the pixel values of the band projection images onto the coordinate positions on the slice plane, which are corrected by the pixel value projecting unit.

17. The tomographic image generation device as claimed in claim 16, wherein the image obtaining unit obtains a radiographic image of the subject taken by applying the radiation to the subject from the given radiation source position,
the pixel value calculating unit generates the band tomographic images by calculating the pixel value at each coordinate position of interest on the slice plane with the pixel values of the band projection images being projected on the corrected coordinate positions,
the frequency synthesis unit performs the frequency synthesis on the generated band tomographic images to generate the tomographic image, and
the tomographic image generation device further comprises a display that displays the radiographic image and the tomographic image.

18. The tomographic image generation device as claimed in claim 1, wherein the pixel value calculation unit calculates weighting factors based on differences between a pixel value at each coordinate position of interest on the slice plane and a pixel value at each coordinate position on each band projection image corresponding to the coordinate positions of interest on the slice plane, and calculates a pixel value at each coordinate position of interest on the slice plane again based on the pixel values of the band projection images and the weighting factors to calculate a new pixel value at each coordinate position of interest on the slice plane.

19. The tomographic image generation device as claimed in claim 18, wherein the pixel value calculation unit iterates calculating a new weighting factor using the new pixel value at the coordinate position of interest on the slice plane, and calculating a new pixel value at the coordinate position of interest on the slice plane again based on the pixel values of the band projection images, the weighting factor, and the new weighting factor.

20. The tomographic image generation device as claimed in claim 1, wherein the frequency decomposition unit, the reconstruction unit, and the frequency synthesis unit generate tomographic images for a plurality of slice planes of the subject, and
wherein the at least one processor is further configured to implement a pseudo image generation unit for generating a pseudo image from the tomographic images.

21. A tomographic image generation method comprising:
obtaining a plurality of projection images corresponding to different radiation source positions, the projection images being taken by moving a radiation source relative to a detector and applying radiation to a subject from the different radiation source positions to which the radiation source is moved;
performing frequency decomposition on each of the projection images to obtain a plurality of band projection images representing frequency components for individual frequency bands for each of the projection images;
reconstructing the band projection images for the individual frequency bands to generate band tomographic images of the subject; and
performing frequency synthesis on the band tomographic images to generate a tomographic image of the subject,
wherein the reconstructing comprises:
projecting pixel values of the band projection images onto coordinate positions of interest on a desired slice plane of the subject based on a positional relationship between each radiation source position during imaging corresponding to the band projection images and the detector, while preserving the pixel values of the band projection images; and calculating a pixel value at each of the coordinate positions of interest on the desired slice plane based on the pixel values of the band projection images projected in a predetermined range relative to each coordinate position of interest on a slice plane to generate the band tomographic images of each slice plane, wherein the projecting pixel values projects, for each of the different radiation source positions, interpolated pixel values at coordinate positions on the band projection images intersecting with straight lines that connect each radiation source position and individual pixel positions on each desired slice plane as pixel values at the individual pixel positions on each desired slice plane on the straight lines.

22. A non-transitory recording medium having recorded thereon a tomographic image generation program for causing a computer to execute operations comprising:

obtaining a plurality of projection images corresponding to different radiation source positions, the projection images being taken by moving a radiation source relative to a detector and applying radiation to a subject from the different radiation source positions to which the radiation source is moved;

performing frequency decomposition on each of the projection images to obtain a plurality of band projection images representing frequency components for individual frequency bands for each of the projection images;

reconstructing the band projection images for the individual frequency bands to generate band tomographic images of the subject; and performing frequency synthesis on the band tomographic images to generate a tomographic image of the subject, wherein the reconstructing comprises:

projecting pixel values of the band projection images onto coordinate positions of interest on a desired slice plane of the subject based on a positional relationship between each radiation source position during imaging corresponding to the band projection images and the detector, while preserving the pixel values of the band projection images; and calculating a pixel value at each of the coordinate positions of interest on the desired slice plane based on the pixel values of the band projection images projected in a predetermined range relative to each coordinate position of interest on a slice plane to generate the band tomographic images of each slice plane, wherein the projecting pixel values projects, for each of the different radiation source positions, interpolated pixel values at coordinate positions on the band projection images intersecting with straight lines that connect each radiation source position and individual pixel positions on each desired slice plane as pixel values at the individual pixel positions on each desired slice plane on the straight lines.

* * * * *